(12) United States Patent
Ouderkirk et al.

(10) Patent No.: US 7,456,805 B2
(45) Date of Patent: Nov. 25, 2008

(54) DISPLAY INCLUDING A SOLID STATE LIGHT DEVICE AND METHOD USING SAME

(75) Inventors: Andrew J. Ouderkirk, Woodbury, MN (US); Michael A. Meis, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 627 days.

(21) Appl. No.: 10/739,792

(22) Filed: Dec. 18, 2003

(65) Prior Publication Data

US 2005/0134527 A1 Jun. 23, 2005

(51) Int. Cl.
*G09G 3/00* (2006.01)
(52) U.S. Cl. ..................... 345/32; 250/461.1
(58) Field of Classification Search .................. 345/32; 359/443, 454; 250/461.1; 353/30, 121
See application file for complete search history.

(56) References Cited

U.S. PATENT DOCUMENTS

| | | | |
|---|---|---|---|
| 3,825,335 A | 7/1974 | Reynolds | |
| 3,902,059 A | 8/1975 | McNamara, Jr. | |
| 4,254,453 A | 3/1981 | Mouyard et al. | |
| 4,386,824 A | 6/1983 | Draper | |
| 4,544,259 A | 10/1985 | Kanaoka et al. | |
| 4,755,918 A | 7/1988 | Pristash et al. | |
| 4,897,771 A | 1/1990 | Parker | |
| 4,914,731 A | 4/1990 | Chen | |
| 4,964,025 A | 10/1990 | Smith | |
| 5,146,248 A | 9/1992 | DuWaer et al. | |
| 5,227,008 A | 7/1993 | Klun et al. | |
| 5,293,437 A | 3/1994 | Nixon | |
| 5,299,222 A | 3/1994 | Shannon et al. | |
| 5,301,090 A | 4/1994 | Hed | |
| 5,302,999 A | 4/1994 | Oshida et al. | |
| 5,317,484 A | 5/1994 | Davenport et al. | |

(Continued)

FOREIGN PATENT DOCUMENTS

DE 199 23 187 A1 11/2000

(Continued)

OTHER PUBLICATIONS

U.S. Appl. No. 10/317,734, filed Dec. 12, 2002, titled "Optical Fiber or Waveguide Lens".

(Continued)

*Primary Examiner*—Ricardo L Osorio
(74) *Attorney, Agent, or Firm*—Jay R. Pralle

(57) ABSTRACT

A display includes a solid state light device and a spatial light modulator in optical communication with the solid state light device. The solid state light device includes an array of solid state radiation sources to generate radiation, where each solid state radiation source includes a controllable radiation output. The solid state light device further includes an array of optical concentrators, where each optical concentrator receives radiation from a corresponding one of the array of solid state radiation sources. The solid state light device further includes a plurality of optical fibers, where each of the plurality of optical fibers includes an input end that receives concentrated radiation from a corresponding optical concentrator. The spatial light modulator includes a plurality of controllable elements operable to modulate light from the solid state light device. The display can be used in a variety of applications.

26 Claims, 12 Drawing Sheets

U.S. PATENT DOCUMENTS

| | | | |
|---|---|---|---|
| 5,337,325 A | 8/1994 | Hwang |
| 5,420,768 A | 5/1995 | Kennedy |
| 5,534,718 A | 7/1996 | Chang |
| 5,567,032 A | 10/1996 | Heizmann |
| 5,574,817 A | 11/1996 | Henson et al. |
| 5,580,471 A | 12/1996 | Fukumoto et al. |
| 5,611,017 A | 3/1997 | Lee et al. |
| 5,629,996 A | 5/1997 | Rizkin et al. |
| 5,634,711 A | 6/1997 | Kennedy et al. |
| 5,661,839 A | 8/1997 | Whitehead |
| 5,693,043 A | 12/1997 | Kittrell et al. |
| 5,709,463 A | 1/1998 | Igram |
| 5,713,654 A | 2/1998 | Scifres |
| 5,727,108 A | 3/1998 | Hed |
| 5,748,816 A | 5/1998 | Jaksic et al. |
| 5,808,794 A | 9/1998 | Weber et al. |
| 5,810,469 A | 9/1998 | Weinrich |
| 5,816,694 A | 10/1998 | Ideker et al. |
| 5,882,774 A | 3/1999 | Jonza et al. |
| 5,886,313 A | 3/1999 | Krause et al. |
| 5,909,037 A | 6/1999 | Rajkomar et al. |
| 5,959,316 A | 9/1999 | Lowry |
| 5,967,653 A | 10/1999 | Miller et al. |
| 6,002,466 A | 12/1999 | Brauch et al. |
| 6,045,240 A | 4/2000 | Hochstein |
| 6,075,595 A | 6/2000 | Malinen |
| 6,104,446 A | 8/2000 | Blankenbecler et al. |
| 6,155,699 A | 12/2000 | Miller et al. |
| 6,172,810 B1 | 1/2001 | Fleming et al. |
| 6,200,134 B1 | 3/2001 | Kovac et al. |
| 6,224,216 B1 | 5/2001 | Parker et al. |
| 6,236,382 B1 | 5/2001 | Kawakami et al. |
| 6,290,382 B1 | 9/2001 | Bourn et al. |
| 6,318,886 B1 | 11/2001 | Stopa et al. |
| 6,340,824 B1 | 1/2002 | Komoto et al. |
| 6,343,872 B1 | 2/2002 | Cerone et al. |
| 6,350,041 B1 | 2/2002 | Tarsa et al. |
| 6,395,564 B1 | 5/2002 | Huang |
| 6,402,347 B1 | 6/2002 | Maas et al. |
| 6,406,172 B1 | 6/2002 | Harbers et al. |
| 6,414,801 B1 | 7/2002 | Roller |
| 6,417,917 B1 | 7/2002 | Jung et al. |
| 6,434,327 B1 | 8/2002 | Gronet et al. |
| 6,521,915 B2 | 2/2003 | Odaki et al. |
| 6,527,411 B1 | 3/2003 | Sayers |
| 6,556,734 B1 | 4/2003 | Bischel et al. |
| 6,560,038 B1 | 5/2003 | Parkyn, Jr. et al. |
| 6,587,573 B1 | 7/2003 | Stam et al. |
| 6,603,258 B1 | 8/2003 | Mueller-Mach et al. |
| 6,692,250 B1 | 2/2004 | Decaudin et al. |
| 6,733,711 B2 | 5/2004 | Durocher et al. |
| 6,809,342 B2 | 10/2004 | Harada |
| 6,821,143 B2 | 11/2004 | Gasquet et al. |
| 6,874,910 B2 | 4/2005 | Sugimoto et al. |
| 6,901,090 B1 | 5/2005 | Ohtsuki |
| 6,943,380 B2 | 9/2005 | Ota et al. |
| 6,949,772 B2 | 9/2005 | Shimizu et al. |
| 6,954,565 B2 | 10/2005 | Lindt |
| 6,960,035 B2 | 11/2005 | Okazaki et al. |
| 7,029,277 B2 | 4/2006 | Gofman et al. |
| 7,091,653 B2 | 8/2006 | Ouderkirk et al. |
| 7,118,438 B2 | 10/2006 | Ouderkirk et al. |
| 7,329,887 B2 * | 2/2008 | Henson et al. .......... 250/494.1 |
| 2001/0001207 A1 | 5/2001 | Shimizu et al. |
| 2001/0009510 A1 | 7/2001 | Lodhie |
| 2001/0010449 A1 | 8/2001 | Chiu et al. |
| 2001/0033712 A1 | 10/2001 | Cox et al. |
| 2002/0018199 A1 | 2/2002 | Blumenfeld et al. |
| 2002/0024055 A1 | 2/2002 | Uemura et al. |
| 2002/0113244 A1 | 8/2002 | Barnett et al. |
| 2002/0126479 A1 | 9/2002 | Zhai et al. |
| 2002/0171047 A1 | 11/2002 | Chan et al. |
| 2002/0176251 A1 | 11/2002 | Plank et al. |
| 2003/0001488 A1 | 1/2003 | Sundahl |
| 2003/0042493 A1 | 3/2003 | Kazakevich |
| 2003/0052594 A1 | 3/2003 | Matsui et al. |
| 2003/0057421 A1 | 3/2003 | Chen |
| 2003/0068113 A1 | 4/2003 | Janz et al. |
| 2003/0091277 A1 | 5/2003 | Mei |
| 2003/0117691 A1 | 6/2003 | Bi et al. |
| 2003/0142500 A1 | 7/2003 | Bachl et al. |
| 2003/0173575 A1 | 9/2003 | Eisert et al. |
| 2003/0175000 A1 | 9/2003 | Caracci et al. |
| 2003/0178627 A1 | 9/2003 | Marchl et al. |
| 2003/0185508 A1 | 10/2003 | Fukuyama et al. |
| 2003/0189829 A1 | 10/2003 | Shimizu et al. |
| 2003/0214571 A1 | 11/2003 | Ishikawa et al. |
| 2003/0233138 A1 | 12/2003 | Spooner |
| 2003/0235800 A1 | 12/2003 | Qadar |
| 2004/0008952 A1 | 1/2004 | Kragl |
| 2004/0106968 A1 | 6/2004 | Yamada |
| 2004/0145913 A1 | 7/2004 | Ouderkirk et al. |
| 2004/0159900 A1 | 8/2004 | Ouderkirk et al. |
| 2004/0164325 A1 | 8/2004 | Siegel |
| 2004/0166249 A1 | 8/2004 | Siegel |
| 2004/0190573 A1 | 9/2004 | Kruschwitz et al. |
| 2004/0262053 A1 | 12/2004 | Ludewig et al. |
| 2005/0153751 A1 | 7/2005 | Bultan |
| 2005/0162737 A1 * | 7/2005 | Whitehead et al. .......... 359/454 |
| 2005/0177208 A1 | 8/2005 | Irwin |
| 2006/0044531 A1 | 3/2006 | Potekev |

FOREIGN PATENT DOCUMENTS

| | | |
|---|---|---|
| DE | 201 11 814 U1 | 12/2001 |
| DE | 10025563 | 12/2001 |
| DE | 201 20 770 U1 | 5/2002 |
| DE | 101 10 835 A1 | 9/2002 |
| DE | 101 34 381 A1 | 1/2003 |
| DE | 101 62 404 A1 | 7/2003 |
| EP | 0 181 193 A | 5/1986 |
| EP | 0 249 934 A | 12/1987 |
| EP | 0 303 741 | 2/1989 |
| EP | 0303741 | 2/1989 |
| EP | 0338641 A1 | 10/1989 |
| EP | 0490 292 A | 6/1992 |
| EP | 0588040 A2 | 3/1994 |
| EP | 0 468 319 | 5/1996 |
| EP | 0889495 A1 | 1/1999 |
| EP | 1 067 332 A2 | 1/2001 |
| EP | 1 081 771 | 3/2001 |
| EP | 1108949 | 6/2001 |
| EP | 1 241 510 | 9/2002 |
| EP | 1 241 869 A | 9/2002 |
| EP | 1 260 196 A2 | 11/2002 |
| EP | 1 372 008 | 12/2003 |
| FR | 2662896 | 12/1991 |
| JP | 02-142695 | 5/1990 |
| JP | 02189803 | 7/1990 |
| JP | 07240536 A | 9/1995 |
| JP | 08008463 | 1/1996 |
| JP | 10256694 | 9/1998 |
| JP | 11284233 | 10/1999 |
| JP | 2002-065603 A | 3/2002 |
| WO | WO 95/20811 | 8/1995 |
| WO | WO 99/41785 | 8/1999 |
| WO | WO 01/20398 A | 3/2001 |
| WO | WO 01/59360 A1 | 8/2001 |
| WO | WO 02/054129 | 7/2002 |
| WO | WO 02/054129 A1 | 7/2002 |
| WO | WO 02/086972 A1 | 10/2002 |
| WO | WO 03/023857 A2 | 3/2003 |
| WO | WO 03/077013 | 9/2003 |
| WO | WO 03/077013 A2 | 9/2003 |

| | | |
|---|---|---|
| WO | WO 03/096387 A2 | 11/2003 |
| WO | WO 2004/004017 A2 | 1/2004 |
| WO | WO 2004/081475 A2 | 9/2004 |
| WO | WO 2005/062382 A2 | 7/2005 |

OTHER PUBLICATIONS

U.S. Appl. No. 10/670,630, filed Sep. 25, 2003, titled "Lensed Optical Fiber and Method for Making the Same".

U.S. Appl. No. 10/726,222, filed Dec. 2, 2003, titled "Illumination System Using a Plurality of Light Sources".

U.S. Appl. No. 10/726,225, filed Dec. 2, 2003, titled "Solid State Light Device".

U.S. Appl. No. 10/726,244, filed Dec. 2, 2003, titled "Reflective Light Coupler".

U.S. Appl. No. 10/726,248, filed Dec. 2, 2003, titled "Multiple LED Source and Method for Assembling same".

U.S. Appl. No. 10/726,257, filed Dec. 2, 2003, titled "LED Curing Apparatus and Method".

U.S. Appl. No. 10/727,220, filed Dec. 2, 2003, titled "Illumination Assembly".

Hsu, J.T. et al., "Design of multi-chips LED module for lighting application", *Solid State Lighting II, Proceedings of SPIE* (2002), vol. 4776, pp. 26-33.

Žukauskas et al, *Introduction to Solid-State Lighting*, John Wiley & Sons, Inc., New York, 2002, pp. 166-167.

"Solid-State Laser/Fiber Optic Expose Machine," IBM Technical Disclosure Bulletin, IBM Corp. vol. 30, No. 10, New York, Mar. 1, 1988, 249-250.

U.S. Application entitled "Illumination System Using a Plurality of Remote Light Sources", filed on Dec. 2, 2002 having U.S. Appl. No. 60/430,230.

U.S. Application entitled "Methods of Making LED-excited Phosphor-based Light Sources", filed on Jan. 27, 2003, having U.S. Appl. No. 60/443,232.

U.S. Application entitled "LED-excited Phosphor-based Light Sources with Front Illumination", filed on Jan. 27, 2003, having U.S. Appl. No. 60/443,235.

U.S. Application entitled "LED-excited Phosphor-based Light Sources", filed on Jan. 27, 2003, having U.S. Appl. No. 60/443,274.

* cited by examiner

DISPLAY INCLUDING A SOLID STATE LIGHT DEVICE AND METHOD USING SAME

RELATED APPLICATIONS

The present application is related to the following co-owned U.S. Patent Applications: ILLUMINATION SYSTEM USING A PLURALITY OF LIGHT SOURCES, filed Dec. 2, 2003 Ser. No. 10/726,222; REFLECTIVE LIGHT COUPLER, filed Dec. 2, 2003 Ser. No. 10/726,244; MULTIPLE LED SOURCE AND METHOD FOR ASSEMBLING SAME, filed Dec. 2, 2003 Ser. No. 10/726,248; ILLUMINATION ASSEMBLY, filed Dec. 2, 2003 Ser. No. 10/727,220; SOLID STATE LIGHT DEVICE, filed Dec. 2, 2003 Ser. No. 10/726,225; and LED CURING APPARATUS AND METHOD, filed Dec. 2, 2003 Ser. No. 10/726,257.

TECHNICAL FIELD

The present disclosure generally relates to displays. More particularly, the present disclosure relates to a display that includes a solid state light device and one or more spatial light modulators and methods of using same.

BACKGROUND

Traditional projection displays use an electrically powered arc lamp with reflective surfaces and focusing lenses to produce a high intensity beam of light. This light beam is imaged using a spatial light modulator and a series of imaging optical elements. Common spatial light modulators include liquid crystal based systems and electrically controllable micromirror arrays.

Some current alternative approaches generally use a package of high power LEDs as the light source. The light emitted by such a source is directed with the aide of focusing optics into a single optical waveguide, such as a large core plastic optical fiber, that transmits the light to a location that is remote from the source. In yet another approach, the single fiber may be replaced by a bundle of individual optical fibers.

Projection displays often have a much lower dynamic illumination range than is perceptible by the eye. The illumination range is usually described by the contrast ratio of the display, where the contrast ratio is the output in the brightest state compared to the output in the darkest state.

One approach for increasing the contrast ratio of projection displays is to put two spatial light modulators in series. One of these modulators may have equal or lower resolution than the other. The contrast ratio of two modulators in series is approximately equal to the product of the individual modulators.

SUMMARY

The present disclosure provides displays and methods of using such displays.

In one aspect, the present disclosure provides a display that includes a light device. The light device includes an array of solid state radiation sources to generate radiation, where each solid state radiation source includes a controllable radiation output. The light device further includes an array of optical concentrators, where each optical concentrator receives radiation from a corresponding one of the array of solid state radiation sources; and a plurality of optical fibers, where each of the plurality of optical fibers includes an input end and an output end, where each input end receives concentrated radiation from a corresponding concentrator. The display further includes a spatial light modulator in optical communication with the light device, where the spatial light modulator includes a plurality of controllable elements operable to modulate light from the light device.

In another aspect, the present disclosure provides a display that includes a light device. The light device includes an array of LED dies to generate optical radiation. The light device also includes an array of optical concentrators, where each optical concentrator receives illumination from a corresponding one of the array of LED dies; and a plurality of optical fibers, where each of the plurality of optical fibers includes an input end and an output end, where each input end receives concentrated illumination from a corresponding optical concentrator. The display further includes a controller in electrical communication with the light device, where the controller is operable to selectively activate one or more LED dies of the array of LED dies. The display further includes a spatial light modulator in optical communication with the light device, where the spatial light modulator includes a plurality of controllable elements operable to modulate light from the light device.

In another aspect, the present disclosure includes a method for displaying an image having a dynamic range, including providing a light device. The light device includes an array of solid state radiation sources to generate radiation, where each solid state radiation source includes a controllable radiation output. The light device also includes an array of optical concentrators, where each optical concentrator receives radiation from a corresponding one of the array of solid state radiation sources; and a plurality of optical fibers, where each of the plurality of optical fibers includes an input end and an output end. Each input end receives concentrated radiation from a corresponding concentrator. The method further includes controlling the array of solid state radiation sources to have outputs determined by a first set of image data; illuminating a face of a spatial light modulator with light from the array of solid state radiation sources, where the spatial light modulator includes an array of controllable elements; and controlling the transmissivity of the array of controllable elements of the spatial light modulator with a second set of image data.

The above Summary of the present disclosure is not intended to describe each disclosed embodiment or every implementation of the present disclosure. The Figures and the Detailed Description that follow more particularly exemplify illustrative embodiments.

DETAILED DESCRIPTION

Figure 1:
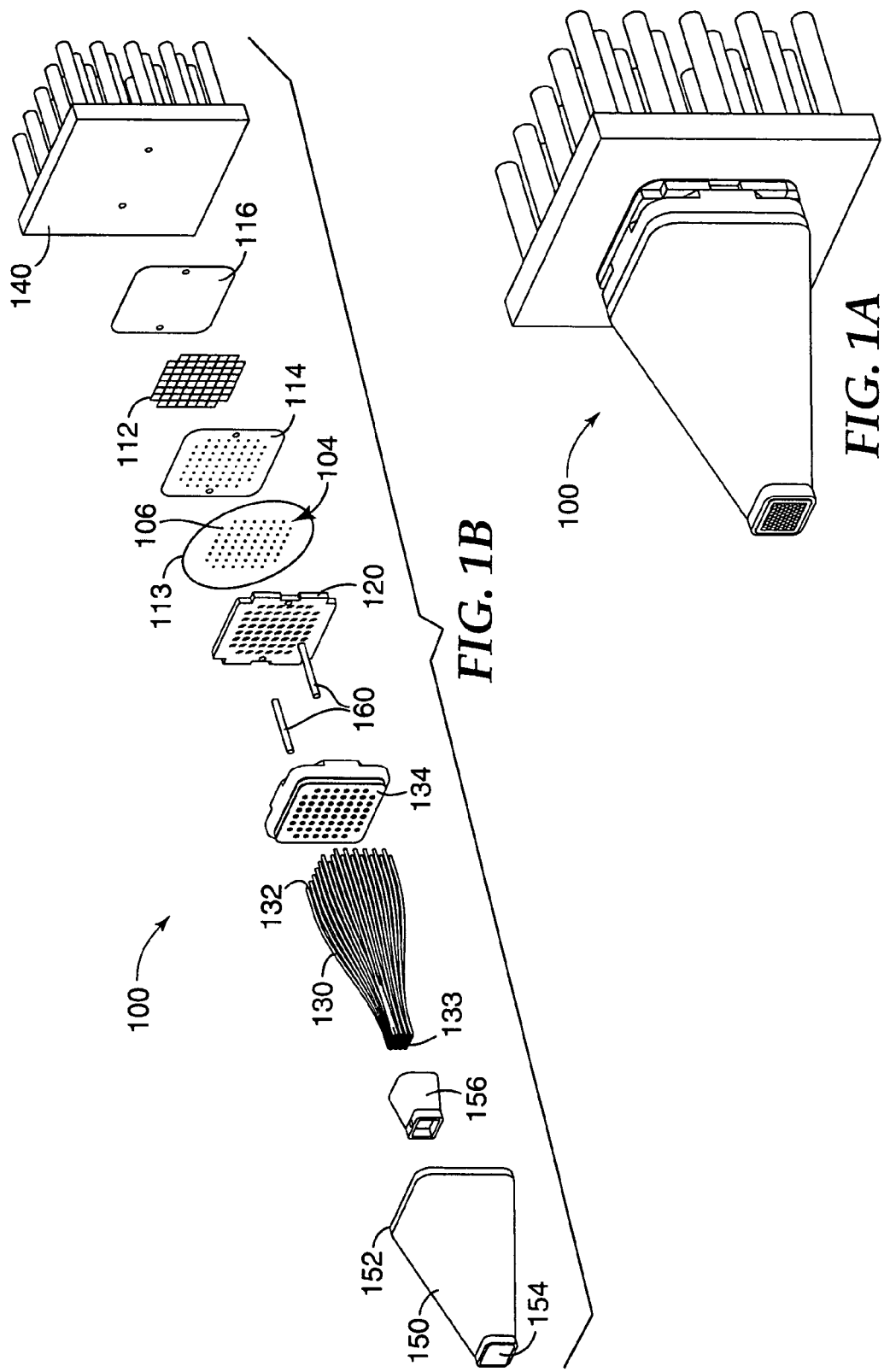
FIG. 1A is a perspective view and FIG. 1B is an exploded view of one embodiment of a solid state light device.

FIG. 1A illustrates an embodiment of a solid state light device 100 (also referred to herein as a light device or photon emitting device). Light device 100 is shown in an exploded view in FIG. 1B. As used herein, the term "light" refers to electromagnetic radiation having a wavelength in the ultraviolet, visible, and/or infrared portion of the electromagnetic spectrum. In the construction described herein, the light device 100 can have an overall compact size comparable to that of a conventional High Intensity Discharge (HID) bulb, thus providing a replacement for a discharge lamp device in various applications including road illumination, region lighting, back lighting, image projection, and radiation activated curing.

Light device 100 includes an array of solid state radiation sources 104 to generate radiation. The radiation is collected and concentrated by a corresponding array of optical concentrators 120. The concentrated radiation is then launched into a corresponding array of waveguides 130, which are supported by an optional support structure 150. Each of these features will now be described in more detail.

The array of solid state radiation sources 104 may include any suitable solid state radiation source. In some embodiments, the array of solid state radiation sources 104 includes discrete LED dies or chips 106 disposed in an array pattern. The discrete LED dies 106 are mounted individually and have independent electrical connections for operational control (rather than an LED array where all the LEDs are connected to each other by their common semiconductor substrate). LED dies 106 can produce a symmetrical radiation pattern and are efficient at converting electrical energy to light. Because many LED dies 106 are not overly temperature sensitive, the LED dies 106 may operate adequately with only a modest heat sink compared to many types of laser diodes. In an exemplary embodiment, each LED die 106 is spaced apart from its nearest neighbor(s) by at least a distance greater than an LED die width. In a further exemplary embodiment, each LED die 106 is spaced apart from its nearest neighbor(s) by at least a distance greater than six LED die widths. These exemplary embodiments provide for suitable thermal management, as explained in further detail herein.

In addition, LED dies 106 can be operated at a temperature from −40° to 125° C. and can have operating lifetimes in the range of 100,000 hours, as compared to most laser diode lifetimes around 10,000 hours or halogen automobile headlamp lifetimes of 500-1000 hours. In an exemplary embodiment, the LED dies 106 can each have an output intensity of about 50 Lumens or more. Discrete high-power LED dies can be GaN-based LED dies commercially available from companies such as Cree (such as Cree's InGaN-based XBright™ products) and Osram. In one exemplary embodiment, an array of LED dies (manufactured by Cree), each having an emitting area of about 300 μm×300 μm, can be used to provide a concentrated (small area, high power) light source. Other light emitting surface shapes such as rectangular or other polygonal shapes can also be utilized. In addition, in alternative embodiments, the emission layer of the LED dies utilized can be located on the top or bottom surface.

In some embodiments, a plurality of bare blue or ultraviolet (UV) LED dies can be utilized, where one or more LED dies can be coated, preferably on a light-emitting surface, with a phosphor layer (not shown), such as YAG:Ce phosphor. The phosphor layer can be used to convert the output of the LED die into "white" light. Phosphor layer placement and construction is described in detail in a co-owned U.S. Patent Application Ser. No. 60/430,230 entitled ILLUMINATION SYSTEM USING A PLURALITY OF LIGHT SOURCES, filed Dec. 2, 2003.

In an alternative embodiment, a collection of red, blue, and green LED dies 106 can be selectively placed in an array. The resulting emission is collected by the array of waveguides 130 so that the light emitted from output ends 133 of the waveguides 130 is seen by an observer as colored light or "white" light, when blended together in concert.

In an alternative embodiment, the array of solid state radiation sources 104 may include a vertical cavity surface emitting laser (VCSEL) array, which can conventionally provide output in the visible region, including "white" light.

As shown in FIG. 1B, the emission from the array of solid state radiation sources 104 is received by an array of optical concentrators 120. In an exemplary embodiment, each optical concentrator receives radiation from a corresponding one of the array of solid state radiation sources 104. In an exemplary embodiment, the array of optical concentrators 120 includes non-imaging optical concentrators (also referred to as reflective optical couplers) disposed in an array. The shape of the reflective surfaces of the array of optical concentrators 120 are designed to capture a substantial portion of the radiation emitted by each of the sources 104 to preserve the power density. In addition, the concentrated output can be designed in a manner to substantially match the acceptance angle criteria of the light receiving waveguides 130 so that a substantial portion of the radiation is useably captured by the waveguides 130 and guided therethrough. In an exemplary embodiment, each non-imaging concentrator of the array of non-imaging concentrators 120 has an interior reflecting surface conforming to a two-dimensional (2-D) surface, with at least a second portion of the interior reflecting surface conforming to a three-dimensional (3-D) surface. This and other reflective surface designs are described in detail in the commonly owned and co-pending U.S. Patent Application Ser. No. 10/726,244 entitled REFLECTIVE LIGHT COUPLER, filed Dec. 2, 2003.

Each optical concentrator in array 120 can be formed, e.g., by injection molding, transfer molding, microreplication, stamping, punching, or thermoforming. The substrate or sheeting in which the array of optical concentrators 120 can be formed (singularly or as part of an array of optical concentrators) can include a variety of materials, such as metal, plastic, thermoplastic material, or multilayer optical film (MOF) (such as Enhanced Specular Reflector (ESR) film available from 3M Company, St. Paul, Minn.). The substrate material used to form the optical concentrator 120 can be coated with a reflective coating, such as silver, aluminum, or reflective multilayer stacks of inorganic thin films, or simply polished in order to increase its reflectivity.

In addition, the optical concentrator substrate can be disposed so that the array of optical concentrators 120 can be oriented beneath, around, or above the LED dies 106. In an exemplary embodiment, the optical concentrator substrate is disposed on or proximate to the array of solid state radiation sources 104 so that each concentrator of array 120 can be formed to slide over each LED die 106, so that the optical concentrator's lower opening 123 (see FIG. 4) provides a close fit around the perimeter of the LED die 106. Alternative concentrator designs include the additional use of a reflective coating on the substrate on which the LED die 106 is supported.

An aspect of the illustrated embodiment of FIG. 1B is the one-to-one correspondence between each radiation source, a corresponding optical concentrator, and a corresponding waveguide. Each optical concentrator surface is designed to convert the isotropic emission from a corresponding LED die, including a phosphor-coated LED die, into a beam that will meet the acceptance angle criteria of a corresponding light-receiving waveguide. As stated above, this concentrator surface design aids in preserving the power density of the light emitted from the LED dies. Referring back to FIG. 1B, the concentrated output radiation is received by a plurality of optical waveguides 130, shown in FIG. 1B as an array of optical fibers, with each waveguide having an input end 132 and an output end 133. The present exemplary embodiment includes an array 130 of large-core (for example, 400 μm to 1000 μm) polymer clad silica fibers (such as those marketed under the trade designation TECS™, available from 3M Company, St. Paul, Minn.). In a further exemplary embodiment, each of the optical fibers 130 can include polymer clad silica fibers having a core diameter of about 600 μm to 650 μm. In exemplary embodiments, the longitudinal lengths of the fibers can be about 1 to 5 inches (2.5 cm-12.5 cm) in length. As the exemplary fibers are very flexible, this short distance still provides the ability to place the fibers in a tight, patterned bundle at the output ends. In addition, the short length provides for a very compact device having a size comparable to the size of conventional HID lamps. Of course, the fiber lengths can be increased in other applications without causing a detrimental effect in operation.

Other types of optical fibers, such as conventional or specialized glass fibers may also be utilized in accordance with the embodiments of the present disclosure, depending on such parameters as, e.g., the output wavelength(s) of the LED die sources. For example, plastic fibers may be susceptible to solarization and/or bleaching with applications involving deep blue or UV light sources.

Alternatively, as would be apparent to one of ordinary skill given the present description, other waveguide types, such as planar waveguides, polymer waveguides, flexible polymer waveguides, or the like, may also be utilized in accordance with the present teachings.

Once the light emitted by the LED die 106 is collected and redirected by the concentrator into the light-receiving fiber, the fiber(s) can be used to transport the light to a specific location with low optical loss by total internal reflection. However, the light receiving fibers do not only serve to transport light; by translating the fibers from the wider spacing of the LED die array to a tighter spacing or spacings at the output aperture, such as a tight packed fiber bundle, light from the (relatively) dispersed LED array can be effectively concentrated into a very small area. Also, the optical design of the exemplary light receiving fiber core and cladding provide for shaping the light beams emerging from the bundled ends due to the Numerical Aperture (NA) of the fibers at the input end as well as the output end. As described herein, the light receiving fibers perform light concentrating and beam shaping, as well as light transportation.

The optical fibers 130 may further include fiber lenses on one or more of the output ends 133 of the optical fibers. Similarly, the input ends 132 of the optical fibers 130 may each further include a fiber lens. Fiber lens manufacture and implementation is described in commonly owned and co-pending U.S. patent application Ser. Nos. 10/317,734 and 10/670,630.

A fiber array connector 134 can be utilized to support the input ends 132 of each optical fiber of array 130. In an exemplary embodiment, the fiber array connector 134 includes a rigid material, such as a molded plastic material, with apertures having a pattern corresponding to the pattern of the array of optical concentrators 120. Each aperture receives the input end 132 of an optical fiber of array 130 and can provide for straightforward bonding thereto.

In an exemplary embodiment, an interconnect circuit layer, rigid or flexible, can be utilized to provide thermal management for and electrical connection to the LED dies 106. As shown in FIG. 1B, the interconnect circuit layer can include a multilayer structure, such as 3M™ Flexible (or Flex) Circuits, available from 3M Company, Saint Paul, Minn. For example, the multilayer interconnect layer can include a metal mounting substrate 112, made, e.g., of copper or other thermally conductive material, an electrically insulative dielectric layer 114, and a patterned conductive layer 113, where the LED dies 106 are operatively connected to bond pads (not shown) of the conductive layer 113. Electrically insulative dielectric layer 114 may include a variety of suitable materials, including polyimide, polyester, polyethylene-terephthalate (PET), polycarbonate, polysulfone, or FR4 epoxy composite, for example. Electrically and thermally conductive layer 113 may include of a variety of suitable materials, including copper, nickel, gold, aluminum, tin, lead, and combinations thereof, for example.

In an exemplary embodiment, and as described in more detail herein, one or more groups of the LED dies 106 are interconnected with each other, but separate from other groupings of LED dies 106, to provide for pixelated radiation output. Vias (not shown) can be used to extend through the dielectric layer 114. The metal mounting substrate 112 can be mounted on a heat sink or heat dissipation assembly 140. The substrate 112 can be separated from heat sink 140 by a layer 116 of electrically insulative and thermally conductive material. In an exemplary embodiment, heat sink 140 can further include a series of thermal conductor pins to further draw heat away from the array of solid state radiation sources 104 during operation.

In one exemplary embodiment, each bare LED die 106 can reside in a recessed portion of the dielectric surface 114, directly on the metal/circuit layer 113. Example implementations of interconnect circuitry are described in a currently pending and co-owned U.S. Patent Application Ser. No. 10/727,220 entitled ILLUMINATION ASSEMBLY, filed Dec. 2, 2003.

In another embodiment, a more rigid FR4 epoxy based printed wiring board structure can be utilized for electrical interconnection. In yet another embodiment, a low cost circuit can be prepared by patterning conductive epoxy or conductive ink onto a suitable substrate as required to connect the LED die array.

Light device 100 further includes an optional support structure. In the exemplary embodiment of FIG. 1B, the support structure is configured as a housing 150, having an input aperture 152 and an output aperture 154. The housing 150 provides strain relief for the array of waveguides 130 and can prevent damage to the waveguides 130 from outside sources. In addition, housing 150 can provide a rigid support that is preferred for vehicular applications, such as those described in more detail herein. Optionally, when waveguides 130 are optical fibers, the support structure can further include a banding 156 that is disposed in contact with a perimeter portion of the second ends of waveguides 130. The banding 156 can aid in distributing the output ends 133 of waveguides 130 in a selected output pattern, as is described in further detail below.

In addition, the fiber array connector 134 can include a ridge or indentation to receive the input aperture 152 of housing 150. While the housing 150 may be bonded or otherwise attached to fiber array connector 134, in an exemplary embodiment, the housing 150 is snap fit on fiber array connector 134.

In an exemplary construction technique, the fibers are first loaded into the fiber array connector and bonded to the connector. A fixture (not shown) can be utilized to group fibers in rows to have an ordered grouping. The fixture can include multiple partitions that repeatably position each fiber from the input end to the output end. In addition, the fixture can be designed so that the fibers do not cross over one another and have a predictable location for the output ends. To secure the output end, a rigid or flexible banding, e.g. a polymer material, is utilized to fix the location of the fibers within a desired output pattern. The strain relief/support housing can then be slid over the fibers and banding and secured to the fiber array connector. The banding can be secured within the output aperture of the housing through the use of conventional adhesives or bonding elements. Alternatively, the support structure can include an encapsulate material that is formed throughout and around the fiber bundle(s).

Alternatively, support structure 150 can include an adhesive material, such as a binding epoxy, which can be applied to a portion of the waveguides 130, such that when the adhesive sets, the waveguides are fixed in a desired pattern.

Overall alignment can be provided by one or more alignment pins 160, which can be used to align the housing 150, fiber array connector 134, concentrator array 120, interconnect circuit layer 110, and heat sink 140 together. A series of alignment holes, such as alignment holes 162 shown in FIG. 2, can be formed in each of the aforementioned parts of the device 100 to receive the alignment pins 160. Alignment of the optical concentrator array 120 to the interconnect circuit layer can be accomplished through the use of fiducials (not shown).

Figure 2:
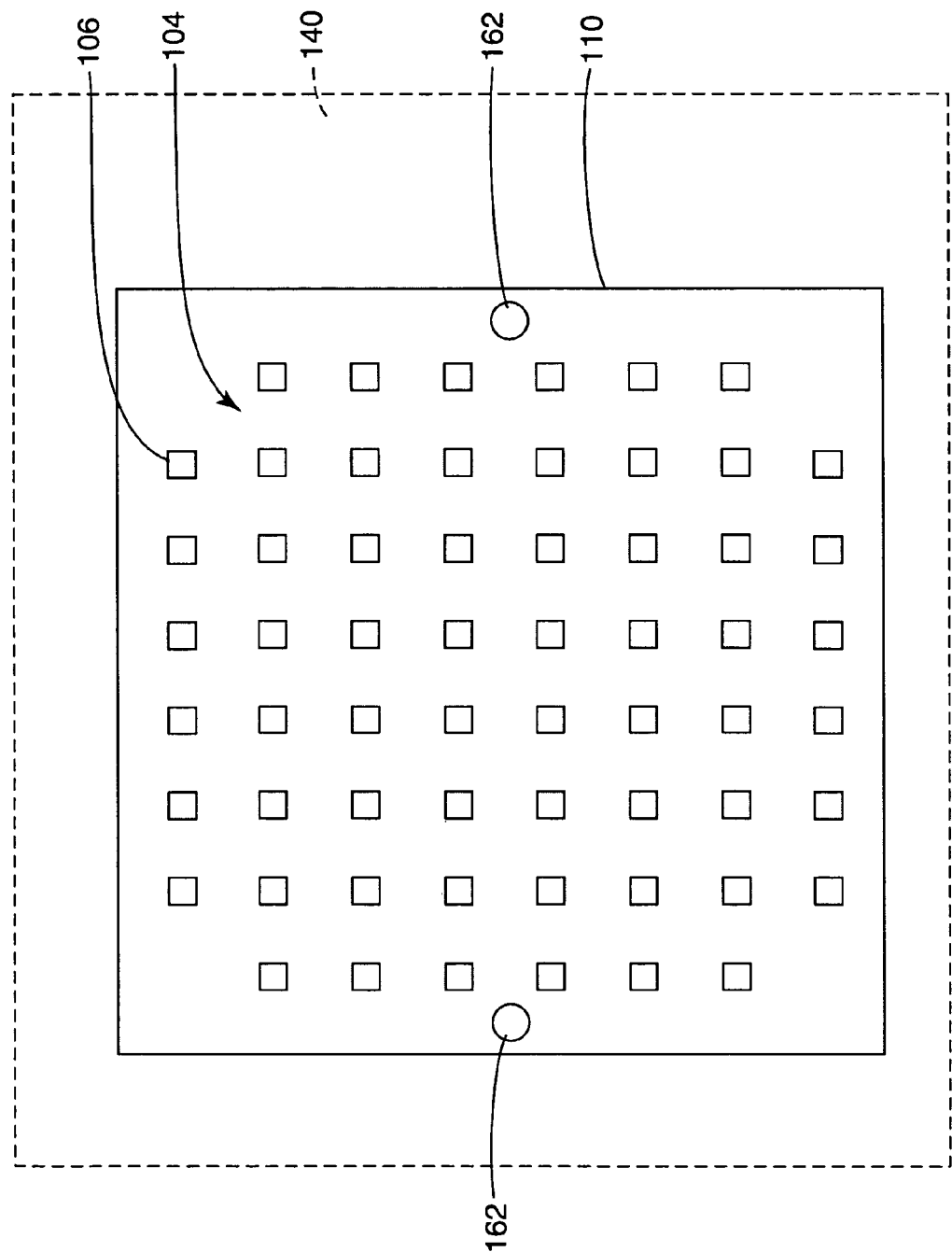
FIG. 2 is a schematic plan view of one embodiment of an LED die array disposed on an interconnect circuit.

FIG. 2 illustrates the footprint of the solid state light device 100. In this exemplary configuration, an array 104 of sixty (60) LED dies 106 can be provided on an interconnect circuit layer 110, which is mounted on heat sink 140, in a substantially rectangular array pattern. Of course, in accordance with the present disclosure, the array of LED dies 106 can include a substantially greater or lesser number of LED dies 106. However, as each LED die 106 has a width of about 300 μm, and each LED die 106 can be spaced from its nearest neighbor by more than a LED die width, the light device 100 of the present disclosure can provide a high overall power density, a compact footprint area (about 1 in$^2$ to 4 in$^2$, or 6.5 cm$^2$ to 26 cm$^2$) and adequate thermal control. In addition, the footprint of the output ends 133 of the fibers 130 (see FIG. 1B) can be even more compact, for example, on the order of about 0.1 in$^2$ to 1 in$^2$ (0.65 cm$^2$ to 6.5 cm$^2$), in exemplary embodiments.

Figure 3:
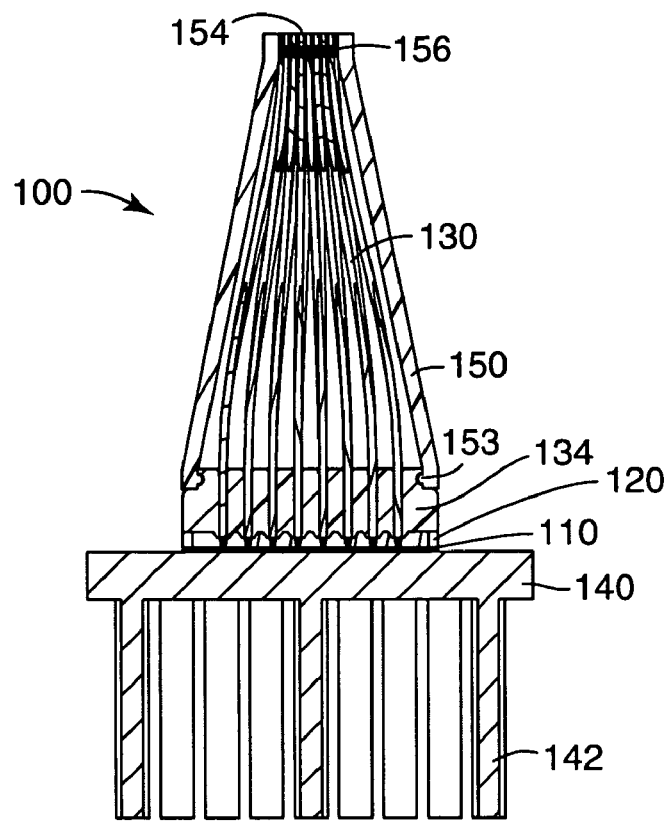
FIG. 3 is a side view of another embodiment of a solid state light device.

A side view of solid state light device 100 is shown in FIG. 3. In this exemplary embodiment, interconnect circuit layer 110 (having LED dies mounted thereon) is disposed on heat sink 140, which further includes heat dissipation pins 142 that extend in an opposite direction from the output aperture 154 of housing 150. In addition, as described herein, the housing 150 can include protrusions 153 to allow for snap fitting onto fiber array connector 134. The array of optical concentrators 120 is disposed between the fiber array connector 134 and the interconnect layer 110. In this embodiment, fibers 130 are supported by the fiber array connector 134 and the banding 156, which is disposed within the output aperture 154 of housing 150.

Figure 4:
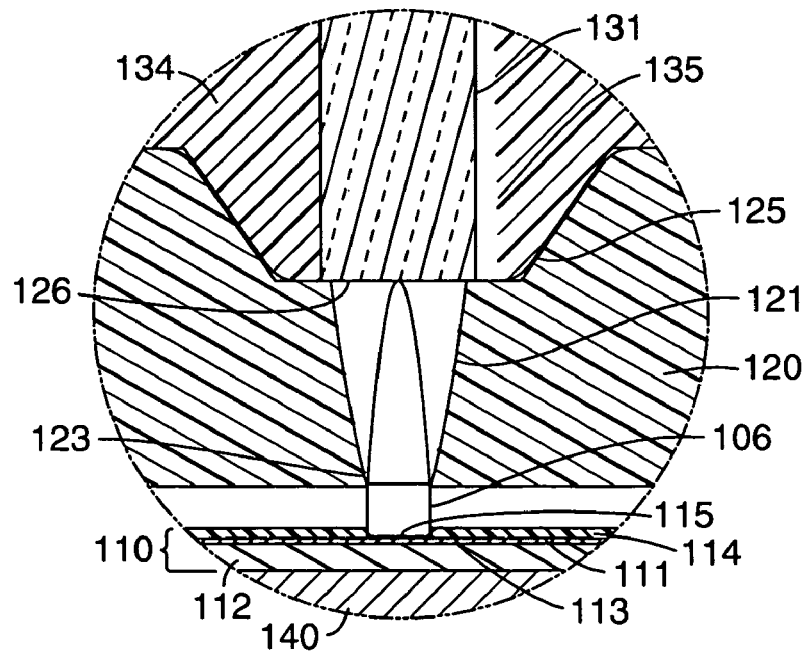
FIG. 4 is a close-up view of another embodiment of an individual LED die coupled to an optical fiber by a non-imaging optical concentrator.

As shown in greater detail in FIG. 4, an exemplary construction of the solid state light device includes a fiber-concentrator alignment mechanism that reduces misalignment between an individual optical fiber 131 of the fiber array and an individual optical concentrator 121 of the concentrator array. In particular, the fiber array connector 134 can further include a protrusion portion 135 that engages in a depression portion 125 of the optical concentrator array substrate. Thus, fiber 131 is received in an aperture of the fiber array connector 134. The fiber array connector 134 is then disposed on the optical concentrator substrate such that protrusion 135 is received by depression 125. In this manner, the output aperture 126 of optical concentrator 121 can be substantially flush with the input end of fiber 131. In addition, with this exemplary design, multiple input ends of the fibers 130 can be polished at the same time so that the fiber ends are positioned with respect to the array of optical concentrators. In addition, in the example construction of FIG. 4, the receiving aperture 123 of optical concentrator 121 can be disposed to be proximate to or to surround the perimeter of an emission surface of a corresponding LED die 106. Although not shown, spacers located between the optical concentrator substrate and the interconnect circuit layer can set the proper spacing between these two components. The optical concentrator substrate can then be affixed to the spacers or otherwise bonded to the interconnect circuit layer using conventional techniques.

FIG. 4 further shows a cross section of an exemplary multiple layer interconnect 110, which includes a conductive epoxy 115 to bond LED die 106 interconnect layer 110. First and second electrically conductive layers 113, 111 (that can include, e.g., nickel and gold, or other conductive materials), provide electrical traces to each LED die 106 in the array, with dielectric layer 114 (e.g., polyimide) disposed to provide electrical insulation. A substrate 112 (e.g., copper) is provided to support the conductive and insulating layers, as well as to provide thermal conductivity to the heat sink 140 to conduct heat away from the direction of emission.

Figure 5A:
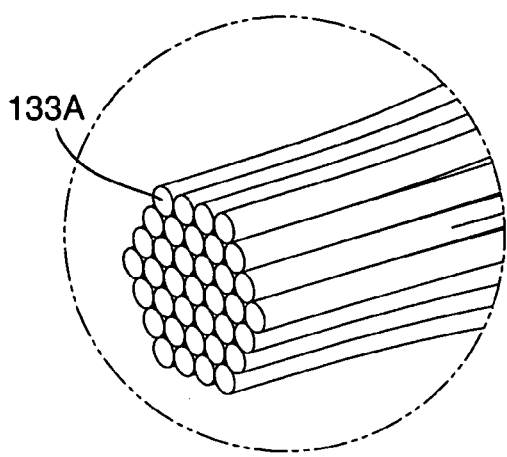
FIGS. 5A-5F are alternative embodiments of fiber output patterns of a solid state light device.
Figure 5B:
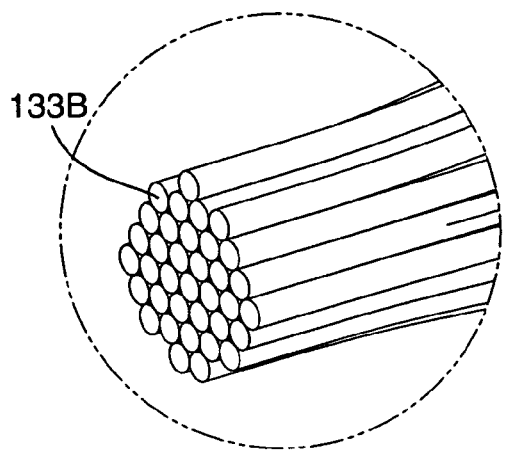
Figure 5C:
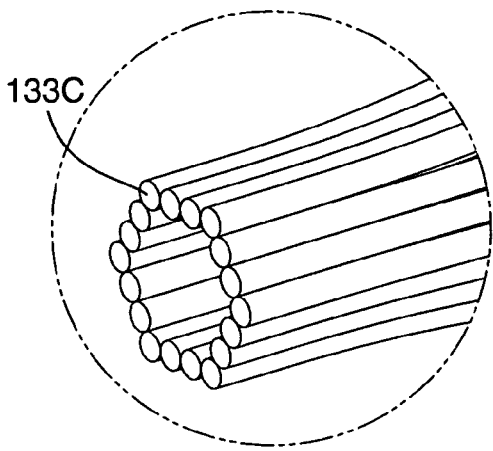
Figure 5D:
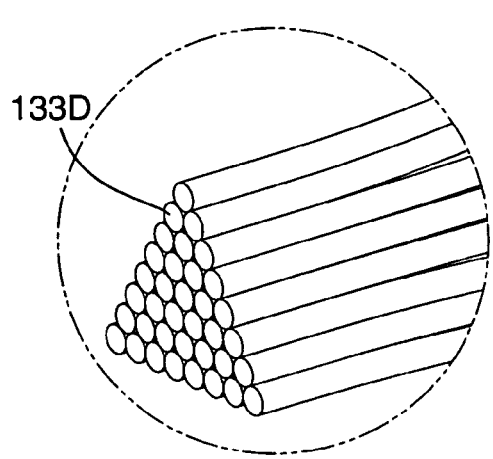
Figure 5E:
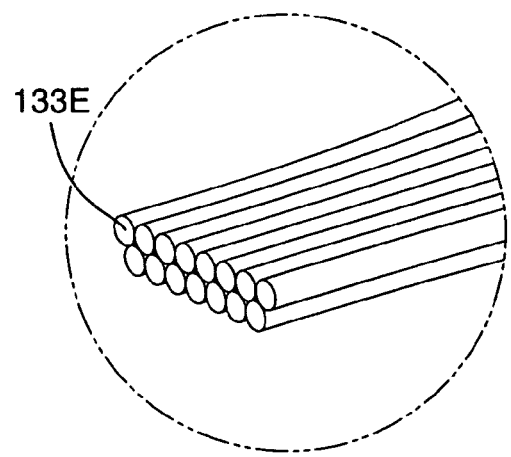
Figure 5F:
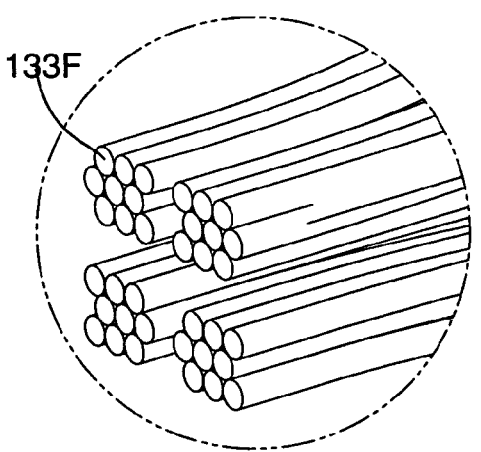

In accordance with the principles described herein, the solid state light device can provide a highly directional and/or shaped output emission, in one or more directions simultaneously. As shown in FIGS. 1A and 1B, the output ends 133 of fiber array 130 can be patterned to provide a rectangular or square output. FIGS. 5A-5F illustrate alternative reconfigurable output end patterns for the fiber array that can be employed depending on the type of illumination that is required for a particular application. For example, FIG. 5A shows a hexagonal output fiber pattern 133A, FIG. 5B shows a circular output fiber pattern 133B, FIG. 5C shows a ring-shaped output fiber pattern 133C, FIG. 5D shows a triangular output fiber pattern 133D, and FIG. 5E shows a line-shaped output fiber pattern 133E. In addition, as shown in FIG. 5F, in an alternative exemplary embodiment, a segmented output pattern 133F can be provided, where multiple separate fiber output groupings can be utilized for specific targeted illumination. As the banding that secures the output ends of the fibers can be formed from a material with flexibility, such as lead, tin, and zinc-based materials and alloys, in some applications, the fiber output pattern can be reconfigurable.

Figure 6A:
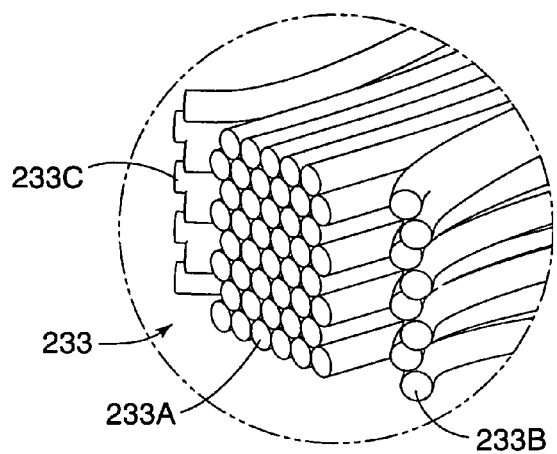
FIG. 6A is an embodiment of an alternative fiber output pattern for a steerable output, and FIGS. 6B and 6C respectively are alternative embodiments of banding and support structure implementations for a steerable output.
Figure 6B:
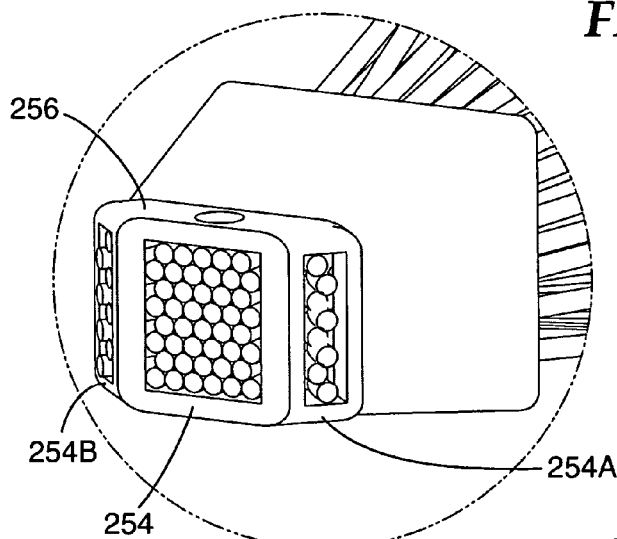
Figure 6C:
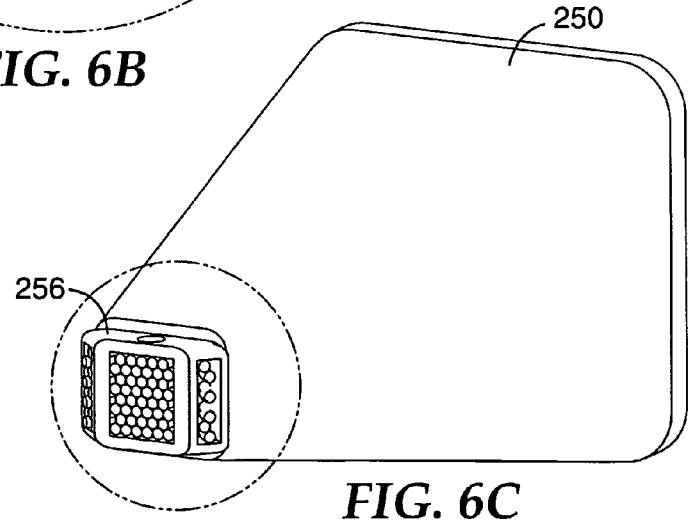

As shown in FIGS. 6A-6C, the output of the solid state light device can be steerable, so that one or more different directions can be illuminated simultaneously or alternatively. FIG. 6A shows fiber output ends 233 arranged, e.g., in three different groupings, 233A, 233B, and 233C. For example, when utilized as a vehicular headlight, the solid state light device can provide output illumination in a forward direction through output ends 233A under normal operation. In the event that the vehicle is turning to a side, the LED dies that correspond to the output fibers 233B can be activated (e.g., by a turn signal indicator or by turning the steering wheel a set amount) so that additional illumination can be provided in that side direction through output fibers 233B. Similarly, if turning to the other side, the LED dies which correspond to the output fibers 233C can be activated so that additional illumination can be provided in that other side direction.

Alternatively, a steerable illumination system can be provided utilizing a laterally extended output arrangement of fibers, such as shown in FIG. 5E, whereby the pixelation control circuitry described below (see e.g., FIGS. 9A and 9B) can activate blocks of illuminated fibers from one side to the other, e.g., during a turn. In this manner, the output illumination can be directed towards (or away from) the direction of the turn, depending on the application.

In this manner, a non-mechanical approach can be used to provide steerable output illumination from the solid state light device. Alternatively, as would be apparent to one of ordinary skill in the art given the present description, greater or fewer fiber groupings can be utilized. In addition, the groupings can have a different relative orientation, such as for high beam-low beam output emissions from the same solid state light device.

In FIG. 6B, a construction is shown that can be utilized to stabilize and support the different fiber groupings. For example, a banding 256 is provided at the output ends of the optical fibers. The banding 256 can provide a first aperture 254, a second aperture 254A and a third aperture 254B, where the fibers disposed in apertures 254A and 254B will output light in different directions from the fibers disposed in aperture 254. In addition, as shown in FIG. 6C, the banding 256 can be connected to or integral with housing 250, as part of the support structure for the solid state light device.

Figure 7A:
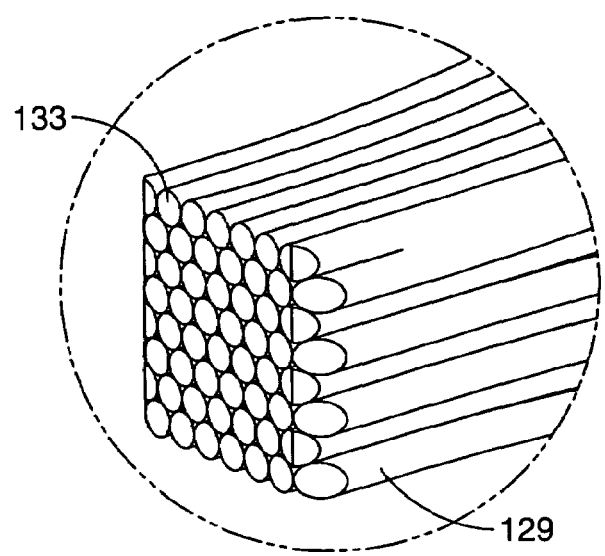
FIG. 7A is an embodiment of a fiber output pattern for a steerable output, where a portion of the output ends of the fibers have angle polished output faces.

Alternatively, as shown in FIG. 7A, the solid state light device can generate steerable light from a single bundle of fiber output ends. For example, fiber output ends 133 can be provided in the same location, such as output aperture 254 from FIG. 6B. In this exemplary embodiment, a portion of these output ends, identified as fiber output ends 129, are angle polished at a different angle, or even substantially different angle (e.g., by 10 to 50 degrees with respect to the fiber axis), than the remainder of fiber output ends 133. The resulting emission will be directed in a different direction from that of the output of fiber ends 133. Thus, similar to the application discussed above with respect to FIGS. 6A-6C, when utilized as a vehicular headlight, the solid state light device can provide output illumination in a both a forward direction (through output ends 133) and a side direction (through output fibers 129).

Figure 7B:
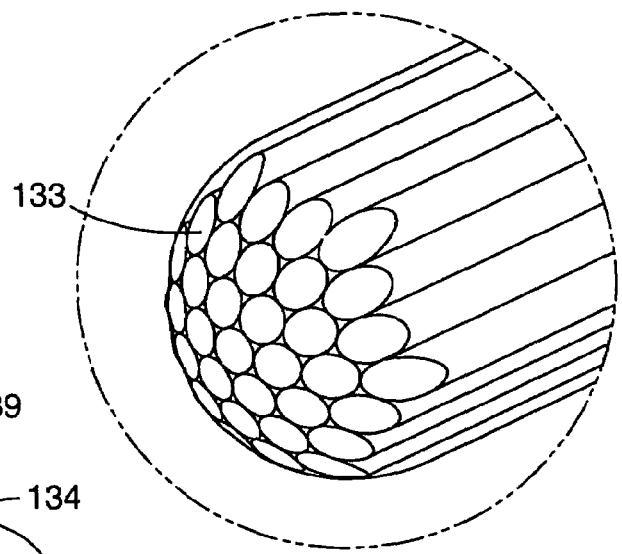
FIG. 7B is another embodiment of a fiber output pattern having output ends that form a curved surface.

The output ends of each fiber may be configured such that they collectively form any suitable shape. For example, FIG. 7B is a schematic diagram of another embodiment of a fiber output end pattern for a solid state light device (e.g., solid state light device 100 of FIG. 1). As shown in FIG. 7B, the fiber bundle includes output ends 133 that have been configured such that the output ends 133 form a curved shape. Any suitable curved shape may be formed, e.g., elliptical, spherical, etc. The output ends 133 may be shaped using any suitable technique, e.g., grinding and polishing.

Figure 13:
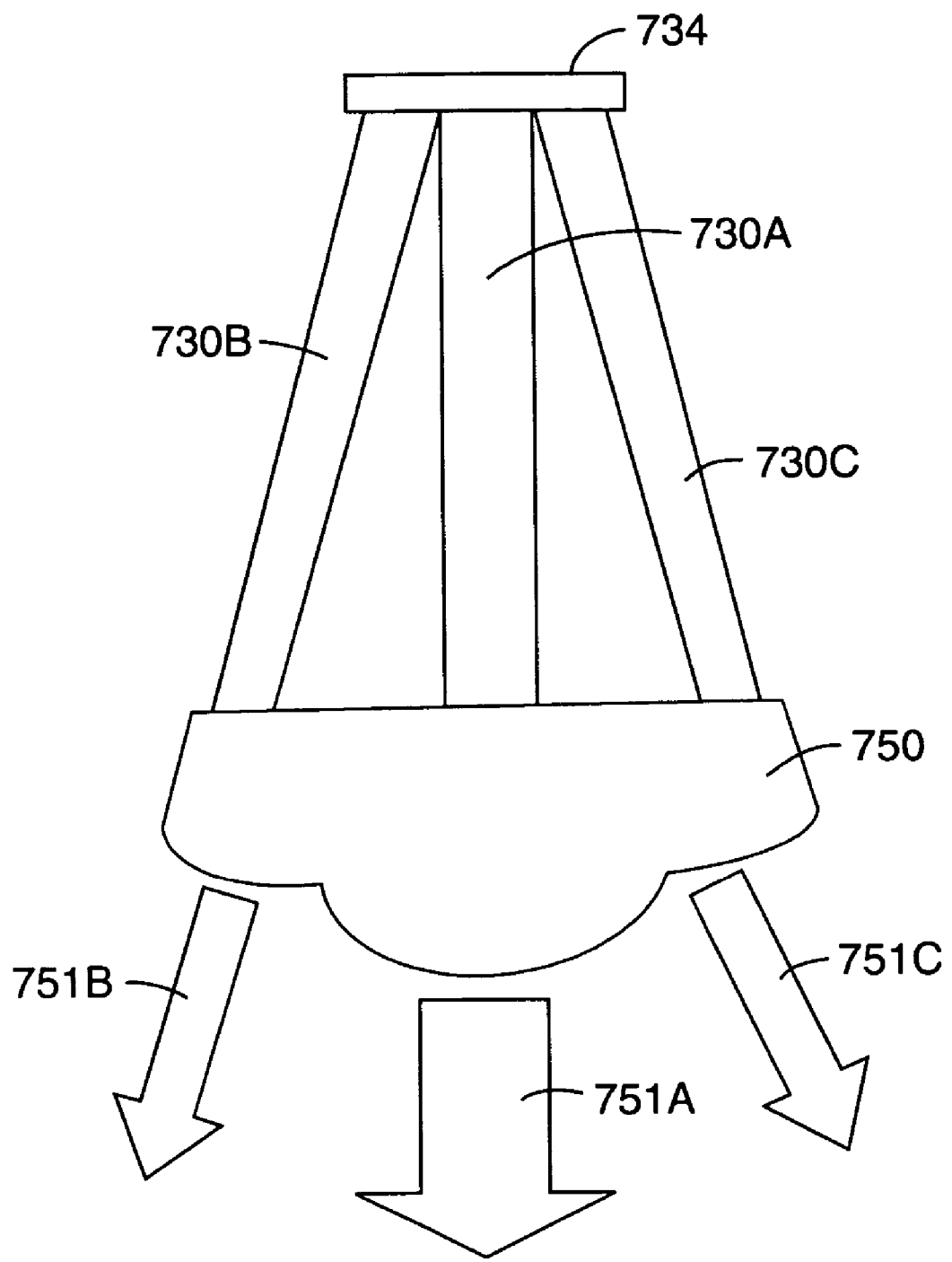
FIG. 13 is an embodiment for a steerable output emission.

In an alternative embodiment to provide steerable illumination, illustrated in FIG. 13, fibers extending from fiber array connector 734 can be bundled into multiple offset fiber bundles, central bundle 730A and side bundles 730B and 730C. Light emitted by the output ends of the fiber bundles is received by a multi-focus lens 750, such as an aspheric lens, that further directs the output from the offset bundles into desired different illumination regions 751A, 751B, and 751C.

Figure 8:
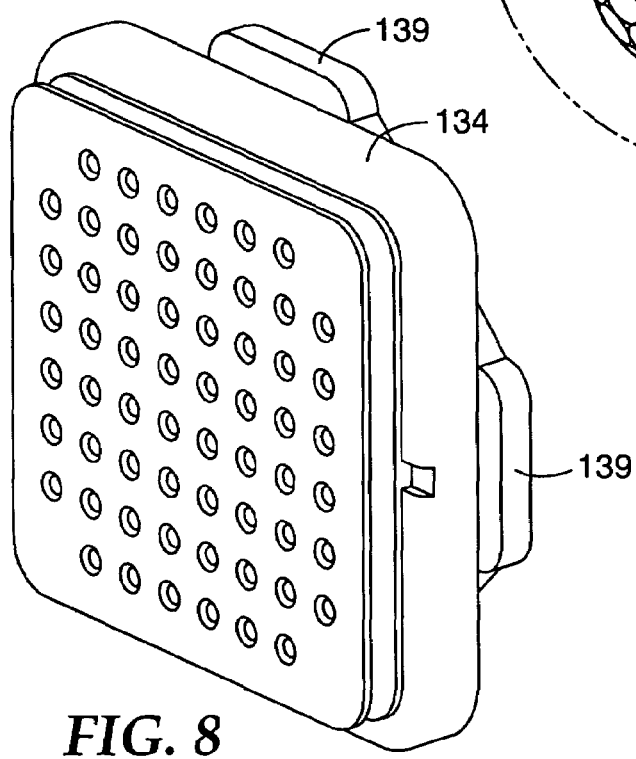
FIG. 8 is an embodiment of a fiber array connector.

In an exemplary embodiment of the present disclosure, the solid state light device can be utilized as an illumination device, such as in a vehicle headlight application. For example, attachment to an existing headlight receptacle can be accomplished through the use of flanges 139, shown in FIG. 8. Flanges 139 can be disposed on the perimeter portion, e.g., of the fiber array connector 134. Each flange can be designed to engage in a locking slot of such a receptacle. Alternatively, the flanges may be formed on other components of the solid state light device, such as the housing or optical concentrator substrate.

Figure 9A:
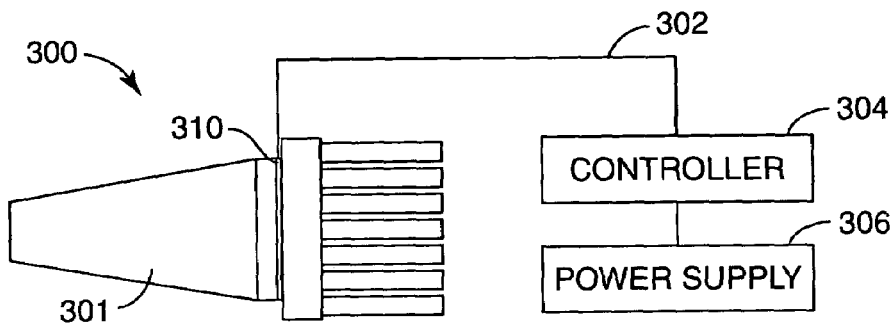
FIG. 9A is an embodiment of a solid state lighting system adapted for pixelation.

According to another embodiment of the present disclosure, as shown in FIG. 9A, an illumination system 300 is provided that allows for pixelated light control that can be used for aperture shaping and/or dynamic beam movement. System 300 includes a solid state light device 301 that is constructed in a manner similar to solid state light device 100 described herein. A controller 304 is in electrical communication with solid state light device 301 via wiring 302 and connector 310, which can be connected to the interconnect circuit layer. A power source 306 is in electrical communication with the controller 304 to provide power/current to the solid state light device 301.

In an exemplary embodiment, controller 304 is configured to selectively activate individual LED dies or groups of LED dies that are contained in solid state light device 301. In addition, as the light receiving waveguides are provided in a one to one correspondence with the LED dies, the illumination system 300 can provide a pixelated output. This type of pixelated control allows for the control of differently colored (e.g., red, green, and blue for RGB output) or similarly colored (e.g., white) LED dies.

Figure 9B:
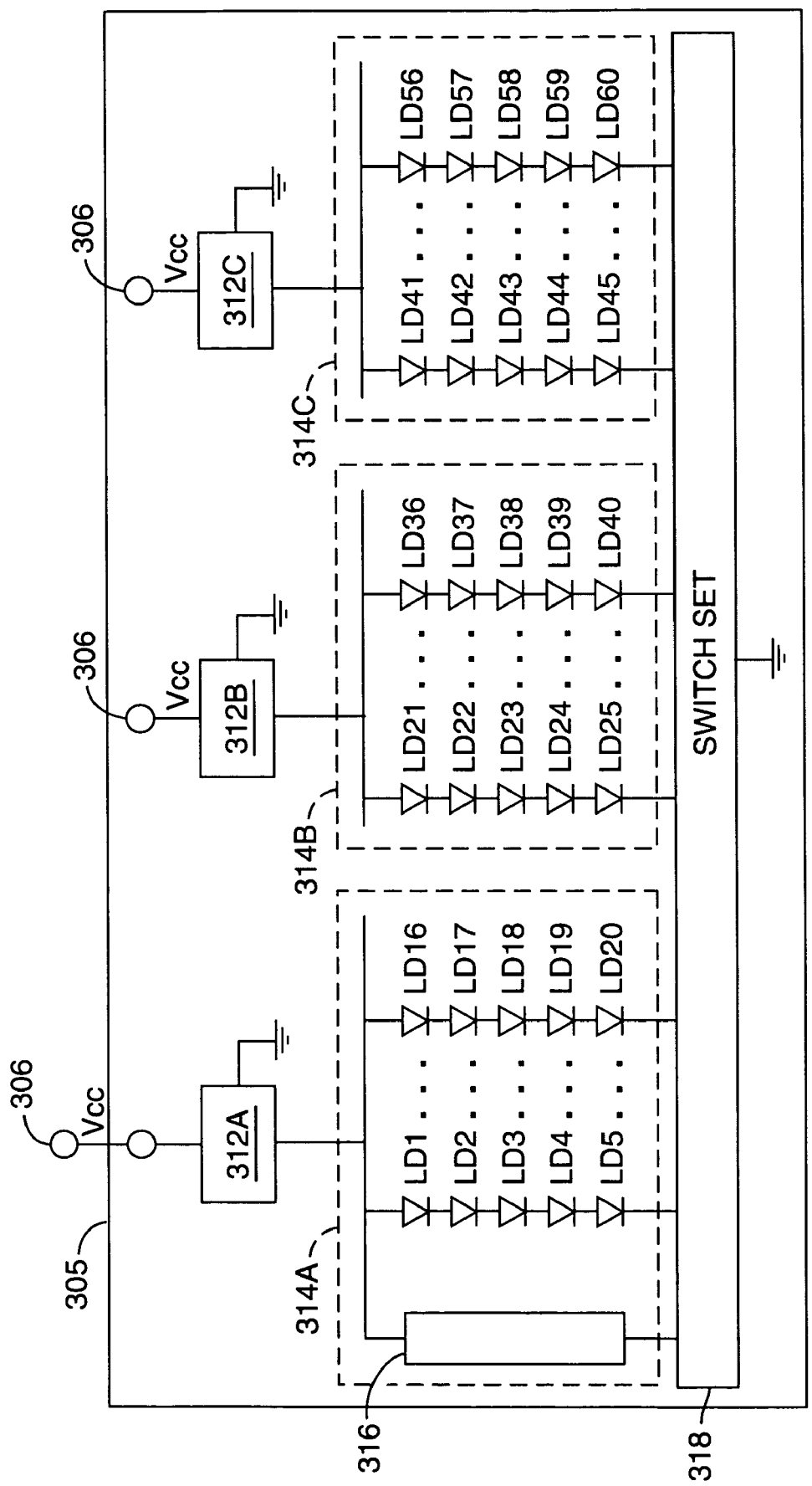
FIG. 9B is an embodiment of a controller circuit adapted for pixelation.

FIG. 9B shows an example control circuit 305 that can provide pixelation to the array of LED dies contained in the solid state light device. In this example, sixty LED dies (LD1-LD60) are provided in the LED die array, which are grouped into three large groupings (314A-314C) of twenty LED dies each, which are each further divided into smaller subgroups or channels (e.g., LD1-LD5) of five LED dies each. Overall, twelve channels of five LED dies each can be separately controlled in this exemplary embodiment. In one example implementation, in an RGB output application, a first grouping of LED dies can include red emitting LED dies, a second grouping of LED dies can include blue emitting LED dies, and a third grouping of LED dies can include green emitting LED dies. Alternatively, in another example implementation, first, second, and third groupings of LED dies can include "white" emitting LED dies.

In addition, the interconnect circuit layer is also designed to provide separate interconnection for the different LED die groupings. Different types of LED die groupings, and greater or lesser numbers of LED dies, can also be utilized in accordance with the principles described herein. With this configuration, separate RGB LED die channels can be driven to provide "white" or other colored output. In addition, should a particular diode channel fail or be dimmed due to LED die deterioration, adjacent channels can be driven at higher currents so that the output illumination appears to remain unchanged. Because of the (relatively) wide LED die spacing and/or the thermal management capabilities of the interconnect layer, greater drive currents to some of the LED die channels will not adversely affect overall performance.

In more detail, a voltage is provided to circuit 305 through power supply 306. The voltage is converted into a regulated output current/voltage supply by boost converter chips 312A-312C and their associated electronics (not shown). In this manner, voltage variations from power source 306 can be mitigated, with the current/voltage supplied to the LED dies being maintained at a regulated level. Chips 312A-312C can include, e.g., LM2733 chips available from National Semiconductor. In this exemplary embodiment, driving voltage/current parameters can be about 20 Volts at 80-100 mA, thus providing a total of about 1.0 to 1.2 A for the entire LED die array. The driving current/voltage is then supplied to the different LED die channels within the array. In this example, each LED die would nominally require about 20 mA bias current, with a bias threshold increasing as the current increases, approaching about 4.0 V. Of course, differing LED die efficiencies or compositions may require differing bias and driving levels.

In addition, a resistor/thermistor chain 316 can be included in circuit 305 to set the overall maximum current for each LED die channel. Further, a switch set 318, including a corresponding number of LED die channel electronic switches, can be provided, whereby each LED die channel is coupled/decoupled to ground in order to activate each particular LED die channel. The switch set 318 can be automatically controlled by a microcontroller (not shown) or a remote switch (e.g., a turn signal), based on the illumination parameters required for a particular application. Of course, this circuit architecture permits many implementations and permutations, as would be understood by one of ordinary skill in the art given the present description. For example, the control circuit 305 can be implemented to drive all LED dies with the same current, or alternatively, a given LED die channel can be turned on/off automatically or on command. By adding a fixed or variable resistance to the switch legs of the switch set, differing currents can be applied to each channel.

Figure 10:
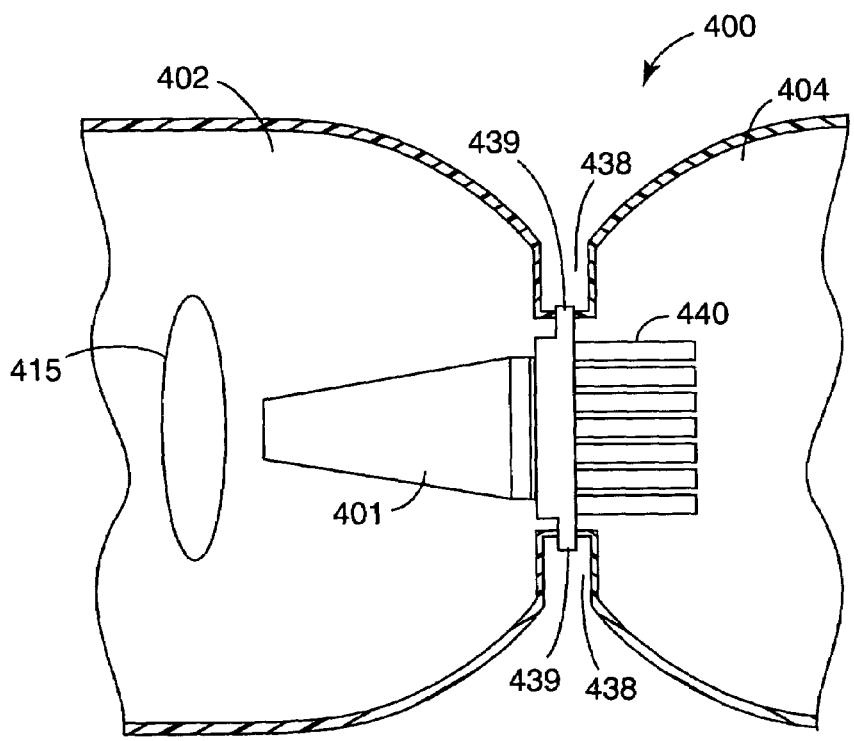
FIG. 10 is an embodiment of an implementation of the solid state light device, here utilized as a "cool" headlight.

FIG. 10 shows a schematic illustration of an exemplary solid state light device 401 utilized in a headlamp application. For example, solid state light device 401, which can be configured in accordance with the embodiments described above, is disposed in a headlight compartment 402 of an automobile or other vehicle (not shown). Light device 401 can be secured in compartment 402 through the use of slidably engaging flanges 439 that are configured to slide and lock within slots 438 of a receptacle. Thus, the heat sink 440, which draws heat away from the direction of light output, is located in a separate compartment 404, such as the interior engine compartment of an automobile or other vehicle. The beam-shaped output illumination can be collected/focused into a requirements-based illumination pattern by an optical element 415. Optical element 415 can be designed to provide a selected output pattern that complies with current safety organization (e.g., NHTSA) standards. Example optical elements can include aspheric/anamorphic optical elements, and/or discontinuous and/or non-analytic (spline) optical elements.

With this approach, the use of complicated reflection optics disposed in headlight compartment 402 can be avoided. In addition, as heat is drawn away from compartment 402, there is no need to specially heat-treat any remaining optical elements in compartment 402, thus avoiding potential performance degradation caused by exposure to continual high intensity heat. Further, if solid state light device 401 is provided with an output fiber and output aperture structure such as shown above in FIGS. 6A-6C, steerable output illumination can be accomplished without having to utilize moving mirror, bulb, and/or lens mechanisms that currently must be employed when steering the output from conventional HID lamps.

Figure 11:
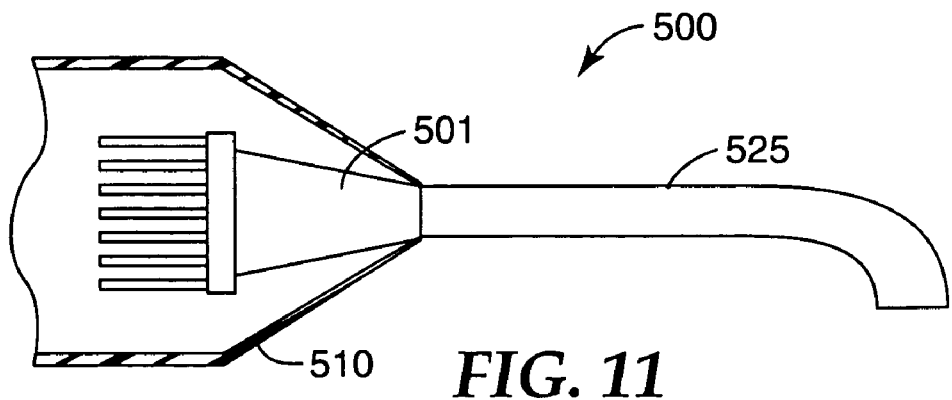
FIG. 11 is another embodiment of an implementation of the solid state light device, here utilized as part of a dental curing apparatus.

The solid state light device described herein may also be utilized in other applications. For example, FIG. 11 is a schematic diagram of a dental curing application, where solid state light device 501 (having a similar construction to that shown in FIGS. 1A and 1B, and/or other embodiments herein) is contained in dental curing apparatus 500. The solid state light device 501 can be disposed in a handle portion 510 of dental curing apparatus 500. In addition, the output fibers used to receive and guide the output from the LED dies or other solid state light generating sources may extend through a light delivery arm 525 that can be placed directly over the curable material. In this application, UV and/or blue radiation sources may be utilized depending on the curing aspects of the materials receiving the illumination.

Figure 12:
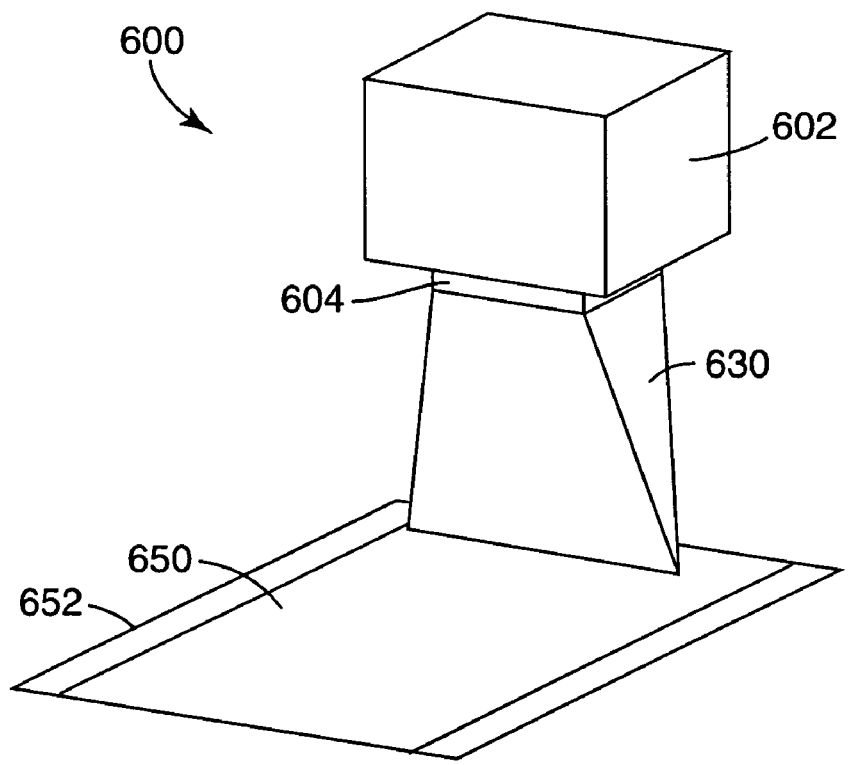
FIG. 12 is another embodiment of an implementation of the solid state light device, here utilized as part of a radiation curing apparatus.

In a further alternative application, FIG. 12 is a schematic diagram of a bulk material curing apparatus, such as a web curing station. For example, in adhesive, tape, or web-based manufacturing, the adhesive agent is often a blue/UV curable material that must be cured to a different material substrate. In conventional methods, high intensity discharge and arc lamps are often utilized to perform the curing process. However, these conventional discharge lamps radiate light and heat in 360 degrees and therefore require complicated heat exchange and/or cooling mechanisms. Alternatively, the substrate material and UV curing agent must be adapted to withstand high intensity heat in some conventional approaches.

FIG. 12 provides a solution to the heating problems found in conventional curing systems, where a curing station 600 includes a solid state light device 604 (constructed similarly to those embodiments described herein), where the heat dissipation or heat sink component of the solid state light device 604 is located in a heat exchange unit 602. As discussed above, heat generated by the radiation sources of the solid state light device 604 is drawn away from the direction of the light output by proper LED die spacing, thermally conductive interconnect circuitry, and/or heat sinks.

In addition, solid state light device 604 can deliver highly concentrated radiation to radiation-curable materials, thus reducing the deleterious effects caused by poor depth of cure. The concentrated output of the LED dies or other radiation-generating source can be collected and guided by the waveguide array, disposed in strain relief housing 630, and delivered to a substrate 650 having a radiation curable material. The substrate 650 can be disposed on a moving platform, substrate film web, or roller belt 652 to provide for continual curing of large quantities of material. As mentioned above with respect to FIGS. 5A-5F, the output ends of the waveguides, e.g. optical fibers, can be arranged in a number of different reconfigurable patterns, thus making the solid state light device particularly suited for curing materials having a wide variety of shapes, and/or curing depth requirements.

In yet another application, the solid state light device described herein can be utilized in a projection system. Because of the ability to provide pixelated output, an LED die array (e.g., array of solid state radiation sources 104 of FIG. 1) can include different output color LED dies for RGB output. In addition, the output can be multiplexed for progressive scanning to provide a suitable projection image. Further, the solid state light device of the embodiments described herein can be utilized as a device for backlighting in LCD displays. In particular, when using phosphor coated dies for "white" emission, pixelated white LED dies can provide an increased contrast ratio for LCD displays.

In embodiments where the solid state light device is used in a display or projection system, the output of individual LED dies or groups of individual LED dies can be selectively controlled, thereby producing controlled light output spatial distributions at the output of the waveguide array. For example, the output of a light device (e.g., solid state light device 100 of FIG. 1) may be imaged onto a spatial light modulator (e.g., an LCD array or array of digital micromirrors), and then imaged onto a front or rear projection screen as is described, e.g., in PCT Patent Publication No. WO 03/077013 A2. The contrast ratio of the image at the projection screen can be increased by modifying the spatial distribution of light produced by the light device. As used herein, the term "contrast ratio" refers to the ratio of intensity of the highest luminance regions of an image and the lowest luminance regions of the same image. For example, regions of a display that should be relatively dark can be obtained by having both the light device and the spatial light modulator be in a relatively dark state. Alternatively, very bright regions can be created in the final display by having high brightness at a region of the light device and the corresponding spatial light modulator.

Figure 14A:
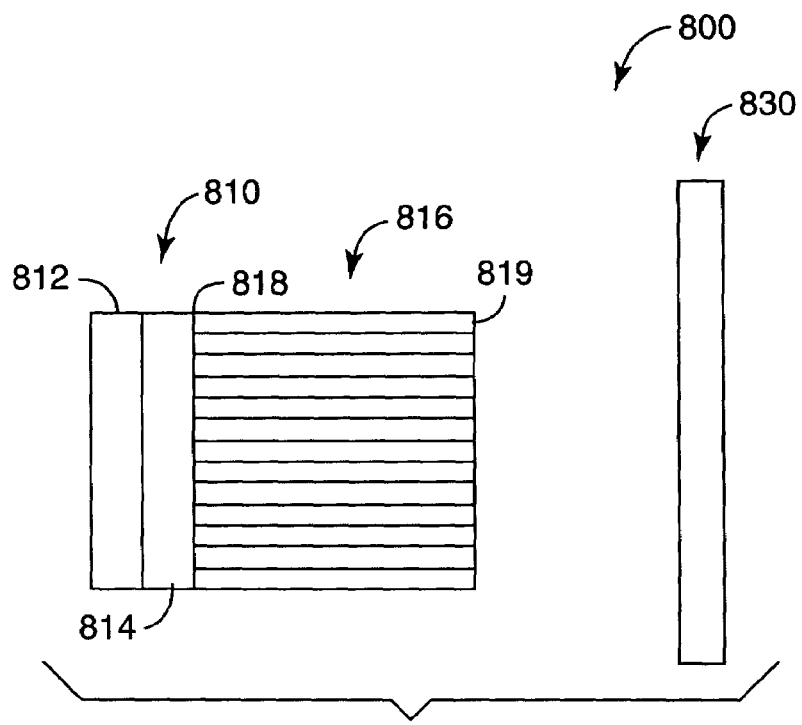
FIG. 14A is a schematic diagram of one embodiment of a display having a light device and a spatial light modulator.

FIG. 14A is schematic diagram of one embodiment of a display 800. As illustrated in FIG. 14A, display 800 includes a light device 810 and a spatial light modulator 830 in optical communication with the light device 810. The light device 810 may be any suitable light device. It may be preferred that light device 810 includes any light device described herein, e.g., light device 100 of FIG. 1B. As shown, light device 810 includes an array of solid state radiation sources 812, an array of optical concentrators 814, and optical fibers 816. Each optical fiber 816 has an input end 818 and an output end 819. All of the design considerations and possibilities described herein with respect to the array of solid state radiation sources 104, the array of optical concentrators 120, and the waveguides 130 of the embodiment illustrated in FIG. 1B apply equally to the array of solid state radiation sources 812, the array of optical concentrators 814, and the optical fibers 816 of the embodiment illustrated in FIG. 14A. It may be preferred that the array of solid state radiation sources 812 includes an array of LED dies as is further described herein.

As is also described herein, the output of each solid state radiation source of the array of solid state radiation sources 812 may be controlled by a controller (e.g., controller 304 of illumination system 300 of FIG. 9A).

In the embodiment illustrated in FIG. 14A, light from the light device 810 is directed toward spatial light modulator 830. Spatial light modulator 830 includes an array of individually addressable controllable elements (i.e., controllable elements 832 of FIG. 14B). Spatial light modulator 830 may include suitable type of controllable element. For example, spatial light modulator 830 may include a variable-transmissivity type of display. In some embodiments, spatial light modulator 830 may include a liquid crystal display (i.e., LCD), which is an example of a transmission-type light modulator. In some embodiments, spatial light modulator 830 may include a deformable mirror device (i.e., DMD), which is an example of a reflection-type light modulator. Display driver circuitry (not shown) can be utilized to control the controllable elements of spatial light modulator 830 according to data that defines an image being displayed. Further, spatial light modulator 830 may include one or more optical elements to further direct light from the modulator 830 to the viewer, e.g., lenses, diffusers, polarizers, filters, beam splitters, etc.

Light device 810 may be located such that the output ends 819 of the optical fibers 816 are in contact with or spaced apart from the spatial light modulator 830. Alternatively, one or more optical elements (not shown) may be positioned between the output ends 819 of the light device 810 and the spatial light modulator 830.

Light that has been modulated by the spatial light modulator 830 can then be directed to a viewer located at a viewing position. In some embodiments, spatial light modulator 830 may direct an image onto a rear-projection screen using any suitable optical system as is further described herein. Alternatively, spatial light modulator 830 may provide an image directly to a viewer without first being directed to a screen.

In some embodiments, light modulated by spatial light modulator 830 may be directed to one or more additional spatial light modulators as is described, e.g., in PCT Patent Publication No. WO 03/077013 A2. These one or more additional spatial light modulators may include any suitable types of elements, e.g., spatial light modulators, collimators, diffusers, filters, etc.

In some embodiments, the spatial resolution of the spatial light modulator may be significantly higher than that of the light device. In other words, the number of controllable elements of the spatial light modulator may be greater than the number of solid state radiation sources of the light device.

Figure 14B:
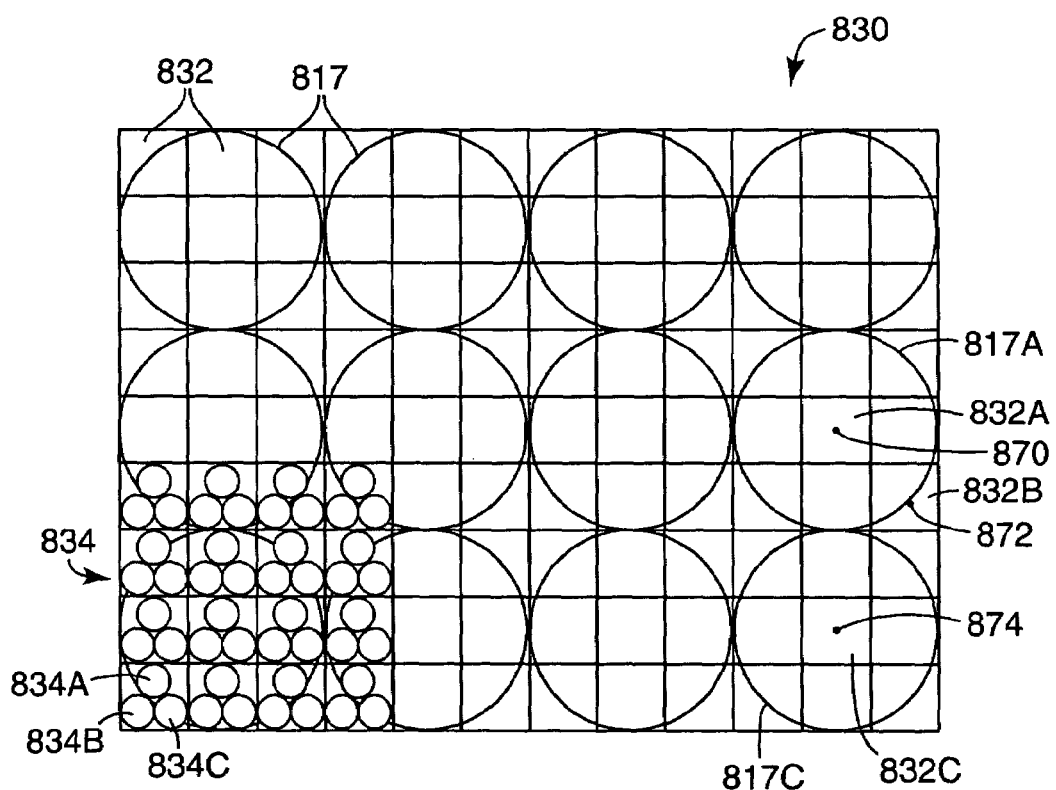
FIG. 14B is a schematic diagram of the spatial light modulator of FIG. 14A.

For example, FIG. 14B is a schematic diagram of the spatial light modulator 830 of the display 800 of FIG. 14A. FIG. 14B shows a plan view of the spatial light modulator 830 and includes an idealized view of the spatial light distribution output 817 (hereinafter referred to as output 817) produced by the output ends 819 of the optical fibers 816 of the light device 810. Spatial light modulator 830 includes controllable elements 832 (e.g., pixels). As illustrated in FIG. 14B, spatial light modulator 830 includes nine controllable elements 832 that correspond to each output 817 from light device 810 (and consequently to each solid state radiation source in the array of solid state radiation sources 812, e.g., LED dies). Any suitable number of controllable elements 832 of spatial light modulator 830 can be provided to correspond to each output 817 of the light device 810.

The size of each output 817 of the lower-resolution light device 810 determines the scale over which one can reliably go from maximum intensity to minimum intensity. For example, to produce a maximum luminance in region 870, output 817A of light device 810 and controllable element 832A of spatial light modulator 830 are set to their maximum-luminance values.

Two different types of regions exist outside of region 870. For example, if region 870 is set at maximum luminance, it is not possible to set the luminance to its minimum value in region 872 because the solid state radiation source of lower-resolution light device 810 that corresponds to output 817A is set at its highest luminance value. In region 874, both the solid state radiation source of light device 810 corresponding to output 817C and the controllable element 832C of the spatial light modulator 830 may be set at their lowest-luminance values. If, for example, each of the light device 810 and the spatial light modulator 830 has a luminance range of 1 to 100 units, then region 870 might have a luminance of 100×100=10,000 units, region 872 would have a luminance of 100×1=100 units, and region 874 would have a luminance of 1×1=1 unit. Such control of the output of the light device 810 and the spatial light modulator 830 may provide a contrast ratio of at least 1000:1. It may be preferred that the display 800 provide a contrast ratio of at least 1500:1. In other words, it may be preferred that a ratio of the luminance of a first point (e.g., region 870), for which the corresponding solid state radiation source (e.g., the source that corresponds to output 817A) is at a maximum light output and the corresponding controllable element (e.g., controllable element 832A) is set to provide maximum illumination, and a second point (e.g., region 874), for which the corresponding solid state radiation source (e.g., the source that corresponds to output 817C) is at minimum light output and the corresponding controllable element (e.g., controllable element 832C) of the spatial light modulator 830 is set to provide minimum illumination, is at least 1000:1. It may be more preferred that a ratio of the luminance of a first point, for which the corresponding solid state radiation source is at a maximum light output and the corresponding controllable element is set to provide maximum illumination, and a second point, for which the corresponding solid state radiation source is at minimum light output and the corresponding controllable element of the spatial light modulator 830 is set to provide minimum illumination, is at least 1501.

Any suitable technique may be utilized for control of both the light device 810 and the spatial light modulator 830 to achieve increased contrast. For example, image data specifying a desired image is supplied to the controller (not shown). The image data indicates a desired luminance for an image area corresponding to each of the controllable elements 832 of the spatial light modulator 830. The controller may set each solid state radiation source of the array of solid state radiation sources 812 (which act as pixels) of the light device 810 to provide an approximation of the desired image using a first set of image data derived from the original image data. This could be accomplished, for example, by determining an average or weighted average of the desired luminance values for the image areas corresponding to each solid state radiation source of the lower-resolution light device 810.

The controller may then set the controllable elements 832 of the spatial light modulator 830 to cause the resulting image to approach the desired image using a second set of image data derived from the original image data. This could be done, for example, by dividing the desired luminance values by the intensity of light incident from the light device 810 on the corresponding controllable elements 832 of the spatial light modulator 830. The intensity of light incident from the light device 810 on a controllable element 832 of spatial light modulator 830 can be computed from the known way that light from each solid state radiation source of the array of solid state radiation sources 812 of the light device 810 is distributed on the spatial light modulator 830. The contributions from one or more of the solid state radiation sources 812 can be summed to determine the intensity with which any controllable element 832 of the higher resolution spatial light modulator 830 will be illuminated for the way in which the solid state radiation sources 812 of the light device 810 are set.

In the embodiment illustrated in FIG. 14B, one or more controllable elements 832 of the spatial light modulator 830 may include three or more sub-pixels 834. Sub-pixels 834 can be independently addressable. Each sub-pixel 834 may be associated with a specific color or colors. For example, sub-pixel 834A may be associated with a red filter or light emitting element, sub-pixel 834B may be associated with a blue filter or light emitting element, and sub-pixel 834C may be associated with a green filter or light emitting element. Any suitable construction of spatial light modulator known in the art may be used to provide color sub-pixels 834.

Figure 15:
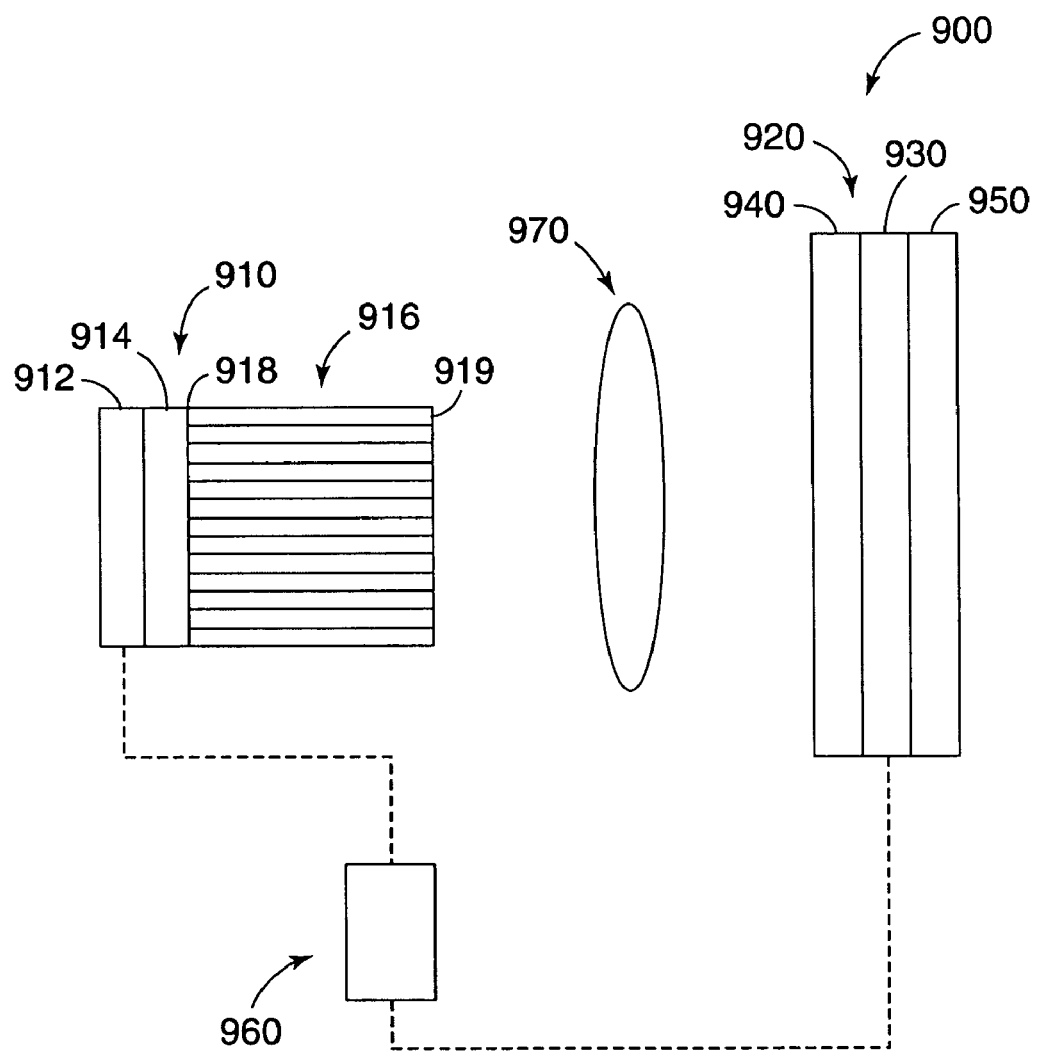
FIG. 15 is a schematic diagram of an embodiment of a rear-projection display having a light device and a spatial light modulator.

The displays of the present disclosure may be used in any suitable display configuration. For example, FIG. 15 is an embodiment of a rear-projection display 900. As shown, display 900 includes a light device 910 and a screen 920 in optical communication with the light device 910. The light device 910 may be any suitable light device described herein (e.g., light device 100 of FIG. 1B). Light device 910 includes an array of solid state radiation sources 912, an array of optical concentrators 914, and optical fibers 916. Optical fibers 916 each have an input end 918 and an output end 919. All of the design considerations and possibilities described herein with respect to the array of solid state radiation sources 104, the array of optical concentrators 120, and the waveguides 130 of the embodiment illustrated in FIG. 1B apply equally to the array of solid state radiation sources 912, the array of optical concentrators 914, and the optical fibers 916 of the embodiment illustrated in FIG. 15. It may be preferred that the array of solid state radiation sources 912 includes an array of LED dies as is further described herein.

In the embodiment illustrated in FIG. 15, light from the light device 910 is directed toward screen 920. Screen 920 includes a spatial light modulator 930, an optional first diffuser 940 in optical communication with the light device 910 and the spatial light modulator 930, and an optional second diffuser 950 in optical communication with the spatial light modulator 930. The spatial light modulator 930 may be integrated with the screen 920; alternatively, the spatial light modulator 930 may be spaced apart from the screen 920. Spatial light modulator 930 includes an array of individually addressable controllable elements (not shown). Spatial light modulator 930 may include any suitable type of controllable elements. For example, spatial light modulator 930 may include a liquid crystal display. Display driver circuitry (not shown in FIG. 15) can be utilized to control the elements of spatial light modulator 930 according to data that defines an image being displayed.

The optional first diffuser 940 may be any suitable diffuser. The first diffuser 940 may cause the intensity of light from the light device 910 that is imaged onto the spatial light modulator 930 to be smoothed out. Alternatively, a similar smoothing effect may be achieved without first diffuser 940 by spacing the spatial light modulator 930 a suitable distance from the light device 910.

The display 900 also includes an optional second diffuser 950. Light modulated by the spatial light modulator 930 is directed through the second diffuser 950, which scatters the outgoing light through a range of directions so that a viewer located on an opposite side of the second diffuser 950 from the spatial light modulator 930 can see light originating from substantially the whole area of screen 920. In general, optional second diffuser 950 may scatter light to a different angular extent in horizontal and vertical planes. Any suitable diffuser known in the art may be used for second diffuser 950.

Display 900 also includes one or more optical elements 970 positioned between light device 910 and screen 920. Any suitable optical element or elements may be used to direct light from the light device 910 to the screen 920, e.g., lenses, diffusers, polarizers, filters, beam splitters, etc.

Display 900 further includes a controller 960 in electrical communication with the light device 910 and the screen 920. The controller 960 may be any suitable controller, e.g., one or more microprocessors running suitable control software. The controller 960 may control the array of solid state radiation sources 912 to provide a low-resolution version of an image to be imaged onto spatial light modulator 930. Controller 960 may also control the controllable elements of spatial light modulator 930 to supply features having a high spatial resolution and to otherwise correct the image provided by the light device 910.

Display 900 may also include calibration mechanisms for compensating for brightness differences between different solid state radiation sources 912 in light device 910. Any suitable calibration mechanism may be utilized, e.g., those mechanisms described in PCT Patent Publication No. WO 03/077013 A2. For example, a light detector or detectors may be moved into different positions for capturing light from different LEDs of the array of LEDs. A controller (e.g., controller 960 of FIG. 15) receives a signal from the light detector. This signal can indicate the brightness of light emitted by each LED for a given current. If the brightness of light emitted by one or more LEDs differs from a desired value, then the controller determines a correction to be applied to the current supplied to each LED. The controller can subsequently apply the correction to one or more LEDs of the array of LEDs.

In some embodiments, light from light device 910 may be directed to one or more additional spatial light modulators as is described, e.g., in PCT Patent Publication No. WO 03/077013 A2. These one or more additional spatial light modulators may include any suitable types of elements, e.g., spatial light modulators, collimators, diffusers, filters, etc.

In some embodiments, each solid state radiation source 912 may be dimmed or turned off during those times when the corresponding controllable elements of spatial light modulator 930 are being refreshed. For example, some spatial light modulators refresh slowly enough that the refresh can be perceived by a viewer. This causes an undesirable effect called "motion blur."

With proper timing, at those times when each row of spatial light modulator 930 is being refreshed, corresponding solid state radiation sources 912 can be turned off or dimmed. At other times the corresponding solid state radiation sources 912 can be overdriven sufficiently that a viewer perceives a desired brightness. The viewers eye cannot perceive rapid flickering of solid state radiation sources 912. Instead, the viewer perceives an average brightness. It is typically desirable to multiplex the operation of the array of solid state radiation sources 912. For example, where LEDs are operated in a multiplexed manner, correcting for motion blur can be performed by synchronizing the multiplexing of the array of solid state radiation devices 912 with the refreshing of spatial light modulator 930.

All references and publications cited herein are expressly incorporated herein by reference in their entirety into this disclosure. Illustrative embodiments of this disclosure are discussed and reference has been made to possible variations within the scope of this disclosure. These and other variations and modifications in the disclosure will be apparent to those skilled in the art without departing from the scope of this disclosure, and it should be understood that this disclosure is not limited to the illustrative embodiments set forth herein. Accordingly, the invention is to be limited only by the claims provided below.

What is claimed is:

1. A display, comprising:
a light device, comprising:
an array of solid state radiation sources to generate radiation, wherein each solid state radiation source comprises a controllable radiation output;
an array of optical concentrators, wherein each optical concentrator receives radiation from a corresponding one of the array of solid state radiation sources; and
a plurality of optical fibers, wherein each of the plurality of optical fibers includes an input end and an output end, wherein each input end receives concentrated radiation from a corresponding concentrator; and
a spatial light modulator in optical communication with the light device, wherein the spatial light modulator comprises a plurality of controllable elements operable to modulate light from the light device.

2. The display of claim 1, wherein the number of controllable elements of the spatial light modulator is greater than the number of solid state radiation sources of the light device.

3. The display of claim 2, wherein each solid state radiation source of the array of solid state radiation sources of the light device is configured to illuminate a plurality of corresponding controllable elements of the spatial light modulator.

4. The display of claim 1, further comprising a diffuser located between the light device and the spatial light modulator, wherein the diffuser is in optical communication with the light device and the spatial light modulator.

5. The display of claim 1, further comprising a diffuser located between the spatial light modulator and a viewing position, wherein the diffuser is in optical communication with the spatial light modulator.

6. The display of claim 1, further comprising one or more additional light modulation stages between the light device and the spatial light modulator.

7. The display of claim 1, further comprising imaging optics configured to image the light device onto the spatial light modulator.

8. The display of claim 7, further comprising a front-projection-type display comprising a display screen configured to reflect light to a viewer.

9. The display of claim 8, wherein the spatial light modulator is integrated with the display screen.

10. The display of claim 1, wherein a ratio of luminance of a first point, for which a corresponding solid state radiation source is at a maximum light output and a corresponding controllable element of the spatial light modulator is set to provide maximum illumination, and a second point, for which the corresponding solid state radiation source is at minimum light output and the corresponding controllable element of the spatial light modulator is set to provide minimum illumination, is at least 1000:1.

11. The display of claim 10, wherein a ratio of luminance of a first point, for which a corresponding solid state radiation source is at a maximum light output and a corresponding controllable element of the spatial light modulator is set to provide maximum illumination, and a second point, for which the corresponding solid state radiation device is at minimum light output and the corresponding controllable element of the spatial light modulator is set to provide minimum illumination, is at least 1500:1.

12. The display of claim 1, wherein the array of solid state radiation sources comprises a plurality of LED dies.

13. The display of claim 12, wherein at least a portion of the plurality of LED dies comprises ultraviolet emitting LED dies.

14. The display of claim 12, wherein at least a portion of the plurality of LED dies comprises white light emitting LED dies.

15. The display of claim 12, wherein a color of light emitted by the LED dies is controllable.

16. The display of claim 1, wherein the plurality of controllable elements of the spatial light modulator comprises variable-transmissivity display elements.

17. The display of claim 16, wherein the variable-transmissivity display elements comprise liquid crystal display elements.

18. The display of claim 1, wherein the spatial light modulator comprises a color spatial light modulator.

19. The display of claim 18, wherein each controllable element of the plurality of controllable elements of the spatial light modulator comprises a plurality of color sub pixels.

20. The display of claim 1, further comprising a controller in electrical communication with the light device and the spatial light modulator, wherein the controller is operable to deliver image data to both the light device and the spatial light modulator.

21. The display of claim 20, wherein the controller is configured to periodically refresh the plurality of controllable elements and to dim or turn off the corresponding solid state radiation source while a controllable element is being refreshed.

22. The display of claim 1, wherein the array of solid state radiation sources is arranged in a regular array.

23. The display of claim 1, wherein each of the plurality of optical fibers comprises a polymer clad silica fiber comprising a core and a cladding, wherein the polymer clad silica fiber further comprises a core diameter of about 250 μm to about 1000 μm.

24. A method for displaying an image having a dynamic range, the method comprising:

providing a light device, comprising:

an array of solid state radiation sources to generate radiation, wherein each solid state radiation source comprises a controllable radiation output;

an array of optical concentrators, wherein each optical concentrator receives radiation from a corresponding one of the array of solid state radiation sources; and a plurality of optical fibers, wherein each of the plurality of optical fibers includes an input end and an output end, wherein each input end receives concentrated radiation from a corresponding concentrator;

controlling the array of solid state radiation sources to have outputs determined by a first set of image data;

illuminating a face of a spatial light modulator with light from the array of solid state radiation sources, wherein the spatial light modulator comprises an array of controllable elements; and controlling the transmissivity of the array of controllable elements of the spatial light modulator with a second set of image data.

25. The method of claim 24, wherein the second set of image data is higher in resolution than the first set of image data.

26. The method of claim 24, wherein the method further comprises:

detecting the controllable radiation output of each solid state radiation source of at least a portion of the array of solid state radiation sources;

comparing the detected controllable radiation output to a desired radiation output; and adjusting the controllable radiation output to the desired radiation output.

* * * * *